(12) United States Patent
Ptacek et al.

(10) Patent No.: US 6,794,187 B2
(45) Date of Patent: Sep. 21, 2004

(54) MASS1 GENE, A TARGET FOR ANTICONVULSANT DRUG DEVELOPMENT

(75) Inventors: Louis J. Ptacek, Salt Lake City, UT (US); H. Steve White, Salt Lake City, UT (US); Ying-Hui Fu, Salt Lake City, UT (US); Shana Skradski, Hillsboro, OR (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 10/220,587

(22) PCT Filed: Mar. 2, 2001

(86) PCT No.: PCT/US01/06962

§ 371 (c)(1),
(2), (4) Date: Sep. 3, 2002

(87) PCT Pub. No.: WO01/65927

PCT Pub. Date: Sep. 13, 2001

(65) Prior Publication Data

US 2003/0208782 A1 Nov. 6, 2003

Related U.S. Application Data

(60) Provisional application No. 60/187,209, filed on Mar. 3, 2000, and provisional application No. 60/222,898, filed on Aug. 3, 2000.

(51) Int. Cl.$^7$ .............................. C12N 5/16; C07H 21/04
(52) U.S. Cl. .................... 435/357; 435/252.3; 536/23.5; 530/350
(58) Field of Search ................................ 435/320, 357, 435/320.1, 252.3, 325; 536/23.5; 530/350; 535/23.5

(56) References Cited

U.S. PATENT DOCUMENTS 5,194,596 A * 3/1993 Tischer et al. .............. 530/399
5,350,836 A * 9/1994 Kopchick et al. ........... 530/399
5,591,630 A * 1/1997 Anderson et al. ........... 435/331

OTHER PUBLICATIONS

Vukicevic et al., 1996, PNAS USA 93:9021–9026.*
Zhao et al., Database EST, Accession No. AQ535714, May 18, 1999, see attached sequence alignment.*
Genbank ACC. No. AZ664090, Dec. 14, 2000, 3 pages.
Levin et al., "Mapping Polymorphism Using PCR Primers Derived From The Sequence of An Avian CR1 Element." Journal of Heredity, 1994, 85 (2), pp. 73–78.
Skradski et al., Genetic Mapping of a Locus (mass 1) Causing Audiogenic Seizures in Mice, Genomics, 1998, 49, 188–192.
Skradski et al., Physical Mapping of MASS1 and Analysis of Candidate Genes for Audiogenic Seizures in Frings Mice. Abstracts of Society for Neuroscience, 1998, 24, 279.12.

* cited by examiner

Primary Examiner—Lorraine Spector
Assistant Examiner—Eileen B. O'Hara
(74) Attorney, Agent, or Firm—Madson & Metcalf

(57) ABSTRACT

The present invention relates to a novel gene which is associated with audiogenic seizures in mice. The gene is known as the Monogenic Audiogenic Seizure-susceptible gene or mass1. The product of the mass1 gene is designated MASS1. Nucleic acid molecules that encode for MASS1 have been identified and purified. The sequence of murine mass1 can be found at SEQ ID NO: 1, and the sequence of human mass1 can be found at SEQ ID NO: 3. Mammalian genes encoding a MASS1 protein are also provided. The invention also provides recombinant vectors comprising nucleic acid molecules that code for a MASS1 protein. These vectors can be plasmids. In certain embodiments, the vectors are prokaryotic or eukaryotic expression vectors. The nucleic acid coding for MASS1 can be linked to a heterologous promoter. The invention also relates to transgenic animals in which one or both alleles of the endogenous mass1 gene is mutated.

34 Claims, 6 Drawing Sheets

```
   1 MTVIFDVSGGPNPPEEDLNPVRGNITFPPGRATVIYNVTYLDDEVPENDELFLIQLESVEGGAEINASRSSVEIIVKKNDSPVNFMQSVYVVPECDHVL
 101 TIPVLRGKDSDGNLIGSDETQVSIRYKVMTWCSTAHAQQNVDFIILQPDITTLVFPPEVHESHLKFQLIDDLIPELAESFHIMIJKNILQGDAVLMCPSTV
 201 QVTIKPNDKPYGVLSFNSILFERPVIIDEDTASSSRPEEIAVVRNGGTHGNVSVSWLTRNSSIPSPVTADITPASGTLQFAQQDMLAPISLYVFDDOLP
 301 EEAPAYLLTIILPHITQGGAEVSEPAQLLFVIQDSINVYGEIAFPPGESQKIESSPSERSLSLSLARRGGSKGDVRVIYSALYIPAQIAMDPLRAKDGILNT
 401 SRRSSLLFPEQNQQVSIKLPIRNDAFLQNGAHFLVQLEAVVLVNIFPPIPPVSPIRFGEIRNISLLVIPAIANCEIQFLSNLPIILHEPEDSSAEVVSIPL
 501 HRDGTDGQATVYWSLRPSGFNSKAVTLDDAGPFNGSVVFLSGGNETSINITVKGGDIPELNETVTLSLIJRVSVDSDVLKSGYTSRDLIILENDDPGGIFE
 601 FSYDSRGPYVIKEGDAVELRITRSRGSLVKQFLRFHVEPRESNEFYGNMGVLEFTPGEREVVITLLTRLDGTPELDEHFWAILSSHGERESKLGRATLVN
 701 ITILKNDYPHGIIEFVSDGLSASIKESKGEDIYHAVYGVIRTRGNFGAVNVSWMSPDFTQDVFPVQGTVCFGQDGEFFKNITVYSLVDEIPEBMEEFTLI
 801 ILLNATGGAQTGIRTTASLBRILRNDDPVYFAEPCVLRVQEGETANFTVLRNGSVDGACTVQYATVDGKASGEEGDFAPVEKCETLVFEVGSRECSISVHVR
 901 DDGIPEIDEPFYIVLENSTGDTVVYEYGVATVIIEANDDPNOVFSLBPIDKAVEEBGKTNAFWLRHRGEPGNWSVAWQLFQNASLQPGQEFYBTSGLVNE
1001 ITDGEETKPVILRAFPDRIPEENEFYILRLVNISGPGGQLAETNEQVTVMPFNDCPFGLFILDPFCLBREVAEDVLSEDDMSYITSFTILRQQGVPGDVR
1101 VGVEVLSREFTAGLPPMIDFILLGSFPSTVPLQPHMRREHSGIDVLYFSGLEGAFGIVIDPKYQPFRNNTIANFTFSAWWMPNANTNGFLIAKDDSHDSIY
1201 YGVKIQTNETHVTLSLHYKTFGSNVTYIAKSTVMKYLBEGVVLHVLIILDDGIIEFYLDGKAMPRGIKSLKGEAITDGPGILRIGAQMDGGARFTGWMQD
1301 VKTYERKLTPEEIYELHAVPARTDLHPISBYLEFRQGESNKSFIVAARDDSBBEGBELFLLKLVSVDGGAQISKENTJARLRIQKSDNSNGLEGFTGACI
1401 PEMFEGSTYACVWERTRGALGYVHVFYTISQIESEGINYLVDDFANASGILIFELPVQRSEVLNLYVLDEDAPELNEYERVTLVSAVPGDGRLGSTPISG
1501 ASIDPEKETTGITVKASDEPYGLMQFSTGLPPQPEDSMSLPASSVPHITVQEEDGEIRLLVIRAQGLLGRVTVGFRTVSLTAFSPEDYQSTAGILEFCSG
1601 ERYKYIFVNITDNSIPELEKSFKVELINLVGQVSDLFRVDGSGSGEBADTDFFLPPVLPHASLGVASQILVTIAASDHAHGVFEFSPESLFVSGTEPEDGY
1701 STVVLNVTRTRQALSAVTLQWKVDSDLDGDLAITSGNITEETGQRIASITVEILPDEEPELDKALTVSILINVSSGSMGVLTNATLTILASDDPYGVFIFP
1801 NKTRPLSVEEATQNVTLSIIRLEGLMGEVAVSYATIDDMEKPPYFPPNLARATQGGDYISASGLALFRANOTEATITISIILDDAEPERSESVFIELENSS
1901 LVDKVQNRPIPHSPRLGPKVBTVAELVIVANCDAFGTVQLSATSVHVAENHVCPIINVTRTGGTFADVSVRFKAVPITAAAGEDYSIASSDVVLLEGETI
2001 KAVPIYIINTXYPELEETELVGLLNETTGGATLGPLREAMITIEASDDPYGLFGFQNTKFIVEEPEFNSVRVSAPIIRNSGTLGNVTVQWWAIINGQFAT
2101 GDLRVVSGNVTFAPGETIQTLLLEVLADIVPELEEVVQVCLAAASGGGTIGLDRVANIVIPANDNPYQSVAFVQSVFRVQEPLERSSYANITVRRSGGHF
2201 GRLLLCYGTSDIDVVARAVEEGEDVLSYYESPTQGVPDPLWRTWWNVSAVEBTQYTCATLCLKERACSAFSVVSGAEGPRCFWMTSWWSGIVNSSDFQFY
2301 KKNMTRVASLPSGQAVACISDYEPVIRQMAVILEGDEFANLTVSVLPTDDAPEMDESFLISLLIEVHLMNISDSFKNQPTIGHPNTSAVVIGLNCDAFGVFIL
2401 YSVSPNTSEDGLCYEVQEQFQFSVELVIYRTGGSLGQVMMEVWRVVGGTATEGLDFMQACDILTEABGETKKMALLTILDDSEPEDNESILVRLYATEGGS
2501 RILPSSDTVTVNILANDNVAGIVSFQTASRSVIGHEGEMLQFHVVRTPPGRGNVTVNVKKVVGQNLEVNFANFTIGOLFEESEGTILNKTIFVHLLDDNIPEEK
2601 EVYQVVLYDVKTQQVSPAGVALLDAQQYAAVLTVEASDEPHGVLNFALSSRFVVLQEANVTIQLFVNREFGOSLGAINVTYATVPGIVSLKNNTEGNLAEP
2701 ESDFIPVVGSLVLEEGETTAAISITYLEDDIPELKEYELVNLIJHVDLIMAPLTSSPPRLGMGLSFMNLLTNCESQRTSLF
```

Fig 6

```
         1  GNITEPPGRATVIYNVTVIDDEVPENDELFLIQER
         2  TTLVEPPFVHESHLKFQIIDDLIEEIAESFHIMEL
         3  GTLQEAQGQMLAPISLVVEDDDLEEEAEAYLLTIL
         4  GSVVELSGQNETSINITVKGDDIEELNETVTLSED
         5  GVLEETPGEREVVITLLTRLDGIEELDEHFWAIES
         6  GTVCEGDQEFFKNITVYSLVDEIEEEMEEFTIIEL
         7  ETLVEEVGSREQSISVHVRDDGIEETDEPFYIVEF
         8  GTVNETDGEETKPVILRAFPDRIEEFNEFYILREV
         9  GTITELPWQRSEVLNLYVLDEDMEELNEYFRVTEV
        10  GTLEEQSGERYKYIFVNITDNSIEELEKSFKVEEL
        11  GNITEETGQRIASITVEIIPDEEEELDKALTVSIL
        12  GLALERANQTEATITISIIDDAEEERSESVFIEEF
        13  SDVVLLEGETTKAVPIYIINDIYELEETFLVQEL
        14  GNVTEAPGETIQTLLLEVIADDVEEIBEVVQVQEA
        15  QWAVILEGDEFANLTVSVIPDDAEEMDESFLISEL
        16  DILTEAEGETKKMAILTIIDDSEEEDNESILVREV
        17  GOLFESEFTLNKTIFVHLLDDNIEEEREVYQVVEY
        18  GSLVLEEGETTAAISITVIEDDIEELREYFLVNET
  Consensus GTLVELEGETEANITVTVIDDDIEELDESFLVVEL
         β1 GTVIEKPGETQKEIRVGIIDDDIFEEDENFLVHES
   G Protein LTLIELDGERERKVSVQIIDDDEPEGQEFFYVFLT
         β2 EEPEEZNDEIVKTISVKVIDDEEYEKNKTFFIEIG
```

Figure 7

SEQUENCE LISTING

<160> NUMBER OF SEQ ID NOS: 33

<210> SEQ ID NO 1
<211> LENGTH: 9437
<212> TYPE: DNA
<213> ORGANISM: Mus musculus

<400> SEQUENCE: 1

| | | | | | | |
|---|---|---|---|---|---|---|
| aatgaacatg | gcattggtgg | tgtggtatga | gccaacagta | ttgaatattc | tgcatgtgtc | 60 |
| aggaggaagg | aagaactctt | gataatatag | tcacaaacct | ttgagacagc | tctcctagct | 120 |
| ctatgaatag | atggttctga | cattgcaccc | ccagagatgt | ccactgctgt | atacatgtct | 180 |
| gcactcaatg | cttcccttat | ccttataccc | tgtgtttcag | ccaccaccca | cggtggcatg | 240 |
| tttcaaagct | gaagttctcc | ctgtttcact | ttttttggtt | ctgaaagtca | ttaacagctg | 300 |
| tatgtcttat | gtgaccttct | gcctgatgcc | gaggcaggtg | tgcatgacaa | gtggtcctag | 360 |
| ggagccggct | tgccccgatg | cttagcttat | ttttgtgacc | tcctgggccc | tgtgagcatt | 420 |
| ttaatctatc | atcttttagc | tgagtagcct | tcaagttcaa | gattcctcag | agcagatgct | 480 |
| ggtagggctg | ggaaaacctg | tttgatgcag | gctttgtttt | tctttacact | gcttttctac | 540 |
| attctcattt | aaaaaaatca | tctatagtat | attggtgcta | ggaatacaca | ctgtaagagt | 600 |
| acaatctgag | ctgatgtgct | gtggcattta | gcgtttctag | ggcggtactt | ttaccaagtc | 660 |
| ctccctctct | ctgattgatc | aatgcctgat | tgtctctgct | cttctcaata | gccctcatca | 720 |
| atctcggtga | ttgagccaag | gagcagaaat | gcatctgtac | ctcttactct | catcagagaa | 780 |
| aaagggacct | atggaatggt | caccgtgact | tttgatgtat | caggtggccc | aaatccccct | 840 |
| gaggaagact | tgaatccagt | tagaggaaat | atcaccttcc | cacctggcag | agcaactgtg | 900 |
| atttacaacg | tgacagttct | tgatgatgag | gtaccagaaa | atgatgaact | attttttgatt | 960 |
| caactgagaa | gtgtagaagg | aggagcagag | attaatgctt | ctaggagctc | ggttgaaatc | 1020 |
| attgtgaaga | aaaatgatag | tcctgtgaac | ttcatgcaga | gtgtttacgt | ggttcccgag | 1080 |
| gacgaccacg | tactcactat | tcccgtgctt | cgtgggaagg | atagtgatgg | aaatctcatt | 1140 |
| ggatctgatg | aaacccaagt | gtcaatcaga | tacaaagtaa | tgacttggga | ttcaacagca | 1200 |
| catgcccagc | aaaacgttga | ctttattgat | cttcagccgg | atactactct | tgtcttttcc | 1260 |
| cctttttgttc | atgaatcaca | cctgaaattt | cagataatcg | atgaccttat | acccagatat | 1320 |
| gctgagtcat | ttcacatcat | gttactaaag | aacaccttac | agggagatgc | tgtgctaatg | 1380 |
| ggcccttcta | cagtacaggt | caccattaag | ccaaatgaca | agccctatgg | agttcttttca | 1440 |
| ttcaatagta | ttttgtttga | agaccagttt | ataattgatg | aagatacagc | atccagttct | 1500 |
| agatttgaag | aaattgcagt | ggttagaaat | ggtggcacac | atgggaatgt | ctctgtgagc | 1560 |
| tgggtgttga | cacggaacag | cagtgatccc | tcaccagtga | ccgcagacat | cacccctgct | 1620 |
| tctgggactc | tgcagttcgc | acaagggcag | atgctggcgc | caatttctct | agtggtcttt | 1680 |
| gacgatgatc | ttccagaaga | ggctgaagct | tacttactta | caatcttgcc | tcacaccata | 1740 |
| caaggaggcg | ctgaagtgag | cgagccagcg | cagcttctgt | tctacattca | ggacagcgat | 1800 |
| aatgtttatg | gagaaatagc | ctttttttcct | ggggaaagcc | agaagattga | aagcagccct | 1860 |
| agtgagcgat | cctatccct | gagtttggcg | agacgtgggg | gaagtaaagg | agacgtgagg | 1920 |
| gtgatttatt | ctgcacttta | tattcctgct | ggagctatgg | accccttgcg | agcaaaagat | 1980 |
| ggcatcttaa | atacatctag | gagaagcagc | ctccttttcc | cagaacagaa | ccaacaagtt | 2040 |

```
tctataaaat taccgataag gaatgatgca ttcctccaga atggggccca cttcctagtg   2100
cagttggaag ctgtggtgtt ggtgaacata ttccctccga ttccaccagt aagtcccaga   2160
ttcggagaaa tcagaaatat ttcattactg gttaccccag ccattgcaaa tggagaaatt   2220
ggctttctta gcaaccttcc aattattttg catgaaccca aagattcttc tgctgaggtg   2280
gtatctatcc ccttgcatcg agatggaact gatggccagg ctaccgtgta ctggagtttg   2340
cggccctctg gctttaattc aaaagcagtg actttggatg acgcaggtcc ttttaatggc   2400
tctgttgtgt tttatctgg acaaaacgaa acatcaatca acattactgt caaaggcgat   2460
gacataccgg agttgaatga aactgtaacc ctttctctag atagggtgag cgtggacagt   2520
gacgtcctaa aatcaggcta tactagccga gacttgatta ttttggaaaa tgatgaccct   2580
ggaggcattt ttgaattttc ttatgattct agaggaccct atgttataaa agaaggagat   2640
gccgtggagc tccggattac tcggtccagg gggtcgcttg ttaaacagtt cctccgcttt   2700
cacgtggaac ccagagagag caatgaattc tatggaaaca tgggggtgct agaattcacc   2760
ccaggagaac gggaagtagt gatcacccctc ctcaccagac tggatggcac accagagttg   2820
gacgagcact tctgggcgat cctcagcagc catggtgaga gagagagcaa gctgggccgt   2880
gctacactcg tcaacataac gattctcaaa aacgactatc ctcatgggat tatagaattt   2940
gtttccgatg gtttgagtgc atcgataaaa gagagcaaag gggaggatat ctatcatgct   3000
gtttatggtg taatacgaac tcgaggcaac tttggtgctg ttaatgtatc atggatggtt   3060
agtccagact ttacgcaaga tgtatttcct gtgcaaggac tgttttgttt tggagaccaa   3120
gaatttttta aaaacatcac tgtctactcc cttgtagatg aaattccaga ggagatggaa   3180
gaattcacca ttatcctact taatgccact ggaggagctc aaacagggat caggacaact   3240
gcctccctga ggattctcag gaacgatgac cccgtttact ttgcagagcc ttgtgttttg   3300
agggtccagg agggtgagac tgccaacttt acagttctca gaaatggatc tgttgacggg   3360
gcctgcactg tccagtatgc taccgtggat gggaaggctt caggagaaga gggagacttc   3420
gctcctgtgg agaagggaga aactcttgtg tttgaagttg gaagcagaga gcagagtata   3480
tctgtacatg tcaaggatga cggaatccca gaaacagatg agccttttta tatagtcctg   3540
ttcaactcaa caggtgacac agtggtttat gagtacgggg tagctacagt cataattgaa   3600
gccaacgatg acccaaatgg tgttttctct ctggagccca tagacaaagc agtggaagaa   3660
ggaaagacaa atgcattttg gatttttacg caccgaggac acttcggcaa tgtttctgtg   3720
gcttggcagc tgttccagaa tgcttctctg cagcctggac aagagttcta tgaaacatca   3780
gggactgtta acttcacaga tggaaaagaa acaaaaccag tcattctccg tgctttccca   3840
gataggattc ctgaattcaa tgaattttat attctaaggc ttgtaaatat ttcaggtcct   3900
ggaggtcaac tagcagaaac caactttcag gtgacagtca tgattccatt caatgacgat   3960
ccgtttggaa ttttcatctt agatccagag tgtctagaga gagaagtagc tgaagatgtc   4020
ctctcagaag acgacatgtc ttacatcacc agcttcacca ttttgagaca cagggtgtc   4080 tttggtgatg tacgggttgg ctgggaagtc ctgtccagag agtttactgc tggccttcca   4140
ccaatgatag actttatact gctaggaagt tttccaagca ctgtgccttt gcaaccacat   4200
atgcgacgtc accacagtgg aacagacgtc ctgtacttca gtggactaga gggtgcattt   4260
gggactgttg atcccaagta ccaacccttc agaaataaca caattgccaa ctttacgttt   4320
tcagcttggg taatgcctaa tgccaacaca aatgggtttc tcatagcaaa ggatgacagt   4380
```

```
catggtagca tctactatgg agtaaaaatc caaacaaatg aaacccacgt gacccttcc     4440
cttcattata aaacttttgg atcaaatgtt acatatattg ccaagagcac tgtcatgaaa    4500
tatttagagg aaggtgtttg gcttcatgtt ttaatcatct tagatgatgg cataattgaa    4560
ttctatctgg acggaaaggc aatgcccaga ggcataaaga gtctgaaagg agaagctatt    4620
actgatggtc ctgggatcct gagaattgga gcagggatgg atggtggtgc cagattcaca    4680
ggttggatgc aggatgtgag gacctatgag cgcaagctga ctcccgagga gatttacgaa    4740
cttcatgctg tgcctgcaag gactgattta cacccgattt ctgggtatct ggagttcaga    4800
caaggagaaa gtaacaagtc gttcattgtt gctgcaagag atgacagtga agaggaagga    4860
gaagaattat tccttcttaa gctggtctct gtggatggtg gggctcagat ttctaaggaa    4920
aacactactg ctcggctaag aatacagaaa agtgacaatg ccaatggcct gtttggcttc    4980
actggggctt gtataccaga gatgacagag gagggtccta ctgtttcctg tgtggttgag    5040
cgaacgaggg gagctctggg ttacgtgcat gtttttctaca ccatctccca gatcgagtca    5100
gaaggcatca attacctcgt tgatgatttt gccaatgcca gtggcactat caccttcttg    5160
ccttggcagc ggtctgaggt cctgaatctg tacgttcttg atgaggacat gcctgagcta    5220
aatgaatatt ttcgggtgac gttggtgtct gcagttccag agatggaaa acttggttca    5280
actcccatca gtggtgccag catagatcct gagaaggaaa ccacaggcat cactgtcaaa    5340
gctagtgacc atccttacgg cttgatgcag ttctccacag ggttgcctcc tcagcctgaa    5400
gattcaatga gtctgcctgc tagcagtgtg ccacatatca cagtgcagga agaggatggc    5460
gaaatccgtt tactggtcat tcgtgcacaa gggctccttg gtcgggtgac tgtaggattt    5520
agaacagtat ccctgacagc atttagtcca gaggactacc agagcactgc tggcacatta    5580
gaatttcaat caggagaaag atataaatat atatttgtca acatcactga taattccatc    5640
cctgaactgg aaaaatcttt taaagttgag ttgttaaact tggatggagg agtgtctgac    5700
ctctttaggg ttgatggcag tgggagtgga gaagcggaca cggatttctt ccttccacct    5760
gtcctcccgc atgccagtct aggagtggct tcccagattc tggtgaccat tgctgcctct    5820
gaccatgctc atggggtgtt tgaattcagc cctgaatcac tcttcgtcag tggaactgaa    5880
ccagaggatg gatacagtac tgtcgtgtta aatgttacac ggactcgggg agccctgtct    5940
gcagtgactt tgcaatggaa ggtagactcg gacctggatg gggatctcgc cattacatct    6000
ggcaacatca catttgagac tgggcagagg attgcttcca tcactgtgga gatactgtca    6060
gatgaagagc cagagctaga caaggcactc accgtgtcga tcctcaacgt gtccagtggc    6120
tccttgggag ttcttacaaa tgccacattg acaattttgg ctagtgatga tccttatggg    6180
gtctttattt ttcctaacaa aactagacct ttgagtgttg aagaagcaac ccagaatgtc    6240
acattatcga taataaggtt gaaaggcctc atgggagaag ttgcagtctc atatgcaacc    6300
atagatgata tggaaaagcc accgtatttc ccacctaatt tagctagagc aactcaagga    6360
ggagattaca tatcagcatc tggattggct cttttcagag ctaatcagac tgaggcaaca    6420
atcactattt caatcctaga tgatgctgaa ccagaacgct cagaatctgt gttcattgaa    6480
cttttcaatt cctctttagt agacaaagta cagaatcgcc caatcccaca ttctccacgc    6540
cttgggccta aggtggagac tgtggcccat ctcgttattg ttgccaatga cgatgcattt    6600
ggaactgtgc agctgtctgc aacatctgtt catgtagcag aaaatcatgt tggacccatt    6660
atcaatgtga ctcgaactgg aggaacattt gcagatgttt ctgttaagtt taaagctgtg    6720
ccaataactg cagcagcggg tgaggactat agtatagcat cttcagacgt ggtcttgctg    6780
```

```
gaaggggaaa ccactaaagc tgtgccaata tatatcatta acgacatcta ccctgagctg    6840
gaagaaacct ttcttgtgca gctactaaac gaaacaacag gtggagccac actggggcct    6900
ctgagagagg cagtcattac catagaggcg tctgatgacc cctacggact gtttggtttt    6960
cagaatacta aatttattgt agaggaacct gagtttaact cagtgagggt aaacgtgcca    7020
ataattcgaa attctgggac actccggcaat gttactgttc aatgggttgc catcattaat    7080
ggacagtttg ctactggcga cctgcgagtt gtctcaggta atgtgacctt tgcccctggg    7140
gaaaccattc aaaccttgtt gttagaggtc ctggctgacg acgttccgga gattgaagag    7200
gttgtccagg tgcaactagc tgctgcctct ggcggaggta caattgggtt agatcgagtg    7260
gcaaatattg ttattcctgc caatgataac ccttacggtt cagtagcctt tgttcagtcc    7320 gttttttcgtg tccaagagcc tctagagaga agttcctatg ctaacataac tgtcaggaga    7380
agcggaggac actttggtcg cctgctgttg tgctatggta cttctgatat tgatgtagtg    7440
gctcgtgcag ttgaggaagg tgaagatgtg ttatcctact atgaatcacc gactcaaggg    7500
gtgcccgacc cactctggag aacttgggtg aacgtgtctg cagtggagga gacacagtat    7560
acctgtgcca ctttgtgtct caaagaacgt gcctgctcag cgttttcagt tgtcagtggt    7620
gccgagggcc ctcggtgctt ctggatgacg tcgtgggtca gcggaactgt gaacagctct    7680
gacttccaaa cctacaagaa gaacatgact agggtggcct ctcttttcag tggccaggca    7740
gttgctggta gtgactacga gcctgtgaca agacagtggg ccgtgatact ggaaggtgat    7800
gagtttgcaa atctcactgt ttctgtactt cctgacgatg ctcccgagat ggatgaaagt    7860
ttcctaattt ctctccttga agttcacctt atgaacatct cagacagttt taaaaaccag    7920
ccaaccatag gacatccgaa tacttccgct gtggtcatag gactgaatgg cgatgccttt    7980
ggagtattca ttatctacag tgttagtccc aatacctcgg aagatggctt atgtgtggaa    8040
gtgcaggaac agccacaaac ttctgtggaa ctggttatct acaggacagg aggcagcctg    8100 ggcaggtca tggtcgaatg gcgcgttgtt ggtggaacgg ctactgaagg tttagatttt    8160
atgggtgctg gagacattct tacttttgca gaaggtgaaa ccaaaaagat ggccatttta    8220 accatttttgg atgattctga gccagaggac aatgaaagca tccttgtccg tctggtggcc    8280
acagagggcg gaagcagaat cctgcccagc tcagacaccg tgacagtcaa catcttggca    8340
aacgacaatg tggcaggaat tgtcagcttt cagacagctt ccagatctgt cataggccac    8400
gaaggagaaa tgttgcagtt ccatgtggta agaacacccc caggtcgagg aaatgtcact    8460
gtcaactgga aagttgttgg acaaaatcta gaagtcaatt ttgctaactt tacgggccaa    8520
ctcttcttct ctgagggtac attgaataaa acaatatttg tacatttgtt ggatgacaat    8580
attcctgagg agaaagaagt ataccaggtt gttctgtatg atgtcaagac ccaaggagtg    8640
tcgccagcag gagttgctct acttgatgcc cagggatatg cagctgtact gacagtggaa    8700
gcaagcgatg agccacacgg tgtttttaaac tttgctctct cctcaagatt tgttgtgctc    8760
caggaggcta atgtaacaat tcagctcttc gtcaacagag agttcggatc tctaggagcc    8820
atcaatgtca cgtatgctac tgttcctgga atagtaagtc tgaaaaacaa cacagaaggc    8880
aacctagcag agccagagtc tgacttcatc cctgtggtgg gctctctggt tttggaggaa    8940
ggggaaacaa cagcagctat cagtatcact gtcctcgagg atgatatacc agagctaaaa    9000
gaatatttct tggtgaattt aactcatgtt gatctcatta tggctcctct gacttcatct    9060
cctcccagac taggtatggg gctctccttt atgaacctt tgactaactg tgagagtcag    9120
```

-continued

```
aggacttcat tgttttaatc agagtgagtt gttatgggaa cgtaacaccg cccottgttt      9180 tgtttgctaa tttcagccat gtgtgaggat gtgatgagca tttagacttg ttctagttag      9240
agactgtcat tgtaagcagt gtaaggcaat aattactctg gtgcttttta aatttttacaa    9300 ctatgttact gccagatatg caacctgcaa ggtggtatta cttttttcaa atgtatttt     9360 ccttcattt cttttaaaat gtaactagct atcttcataa gtcaacagtt ttctttaag      9420 tttaatattt attttgt                                                     9437
```

<210> SEQ ID NO 2
<211> LENGTH: 2780
<212> TYPE: PRT
<213> ORGANISM: Mus musculus

<400> SEQUENCE: 2

```
Met Val Thr Val Thr Phe Asp Val Ser Gly Gly Pro Asn Pro Pro Glu
1               5                   10                  15

Glu Asp Leu Asn Pro Val Arg Gly Asn Ile Thr Phe Pro Pro Gly Arg
            20                  25                  30

Ala Thr Val Ile Tyr Asn Val Thr Val Leu Asp Asp Glu Val Pro Glu
        35                  40                  45

Asn Asp Glu Leu Phe Leu Ile Gln Leu Arg Ser Val Glu Gly Gly Ala
    50                  55                  60

Glu Ile Asn Ala Ser Arg Ser Ser Val Glu Ile Ile Val Lys Lys Asn
65                  70                  75                  80

Asp Ser Pro Val Asn Phe Met Gln Ser Val Tyr Val Pro Glu Asp
                85                  90                  95

Asp His Val Leu Thr Ile Pro Val Leu Arg Gly Lys Asp Ser Asp Gly
            100                 105                 110

Asn Leu Ile Gly Ser Asp Glu Thr Gln Val Ser Ile Arg Tyr Lys Val
        115                 120                 125

Met Thr Trp Asp Ser Thr Ala His Ala Gln Gln Asn Val Asp Phe Ile
    130                 135                 140

Asp Leu Gln Pro Asp Thr Thr Leu Val Phe Pro Pro Phe Val His Glu
145                 150                 155                 160

Ser His Leu Lys Phe Gln Ile Ile Asp Asp Leu Ile Pro Glu Ile Ala
                165                 170                 175

Glu Ser Phe His Ile Met Leu Leu Lys Asn Thr Leu Gln Gly Asp Ala
            180                 185                 190

Val Leu Met Gly Pro Ser Thr Val Gln Val Thr Ile Lys Pro Asn Asp
        195                 200                 205

Lys Pro Tyr Gly Val Leu Ser Phe Asn Ser Ile Leu Phe Glu Arg Pro
    210                 215                 220

Val Ile Ile Asp Glu Asp Thr Ala Ser Ser Arg Phe Glu Glu Ile
225                 230                 235                 240

Ala Val Val Arg Asn Gly Gly Thr His Gly Asn Val Ser Val Ser Trp
                245                 250                 255

Val Leu Thr Arg Asn Ser Ser Asp Pro Ser Val Thr Ala Asp Ile
            260                 265                 270

Thr Pro Ala Ser Gly Thr Leu Gln Phe Ala Gln Gly Gln Met Leu Ala
        275                 280                 285

Pro Ile Ser Leu Val Val Phe Asp Asp Leu Pro Glu Glu Ala Glu
    290                 295                 300

Ala Tyr Leu Leu Thr Ile Leu Pro His Thr Ile Gln Gly Gly Ala Glu
305                 310                 315                 320
```

-continued

```
Val Ser Glu Pro Ala Gln Leu Leu Phe Tyr Ile Gln Asp Ser Asp Asn
                325                 330                 335

Val Tyr Gly Glu Ile Ala Phe Phe Pro Gly Glu Ser Gln Lys Ile Glu
                340                 345                 350

Ser Ser Pro Ser Glu Arg Ser Leu Ser Leu Ser Leu Ala Arg Arg Gly
                355                 360                 365

Gly Ser Lys Gly Asp Val Arg Val Ile Tyr Ser Ala Leu Tyr Ile Pro
                370                 375                 380

Ala Gly Ala Met Asp Pro Leu Arg Ala Lys Asp Gly Ile Leu Asn Thr
385                 390                 395                 400

Ser Arg Arg Ser Ser Leu Leu Phe Pro Glu Gln Asn Gln Val Ser
                405                 410                 415

Ile Lys Leu Pro Ile Arg Asn Asp Ala Phe Leu Gln Asn Gly Ala His
                420                 425                 430

Phe Leu Val Gln Leu Glu Ala Val Val Leu Val Asn Ile Phe Pro Pro
                435                 440                 445

Ile Pro Pro Val Ser Pro Arg Phe Gly Glu Ile Arg Asn Ile Ser Leu
                450                 455                 460

Leu Val Thr Pro Ala Ile Ala Asn Gly Glu Ile Gly Phe Leu Ser Asn
465                 470                 475                 480

Leu Pro Ile Ile Leu His Glu Pro Lys Asp Ser Ser Ala Glu Val Val
                485                 490                 495

Ser Ile Pro Leu His Arg Asp Gly Thr Asp Gly Gln Ala Thr Val Tyr
                500                 505                 510

Trp Ser Leu Arg Pro Ser Gly Phe Asn Ser Lys Ala Val Thr Leu Asp
                515                 520                 525

Asp Ala Gly Pro Phe Asn Gly Ser Val Val Phe Leu Ser Gly Gln Asn
                530                 535                 540

Glu Thr Ser Ile Asn Ile Thr Val Lys Gly Asp Asp Ile Pro Glu Leu
545                 550                 555                 560

Asn Glu Thr Val Thr Leu Ser Leu Asp Arg Val Ser Val Asp Ser Asp
                565                 570                 575

Val Leu Lys Ser Gly Tyr Thr Ser Arg Asp Leu Ile Ile Leu Glu Asn
                580                 585                 590

Asp Asp Pro Gly Gly Ile Phe Glu Phe Ser Tyr Asp Ser Arg Gly Pro
                595                 600                 605

Tyr Val Ile Lys Glu Gly Asp Ala Val Glu Leu Arg Ile Thr Arg Ser
                610                 615                 620

Arg Gly Ser Leu Val Lys Gln Phe Leu Arg Phe His Val Glu Pro Arg
625                 630                 635                 640

Glu Ser Asn Glu Phe Tyr Gly Asn Met Gly Val Leu Glu Phe Thr Pro
                645                 650                 655

Gly Glu Arg Glu Val Val Ile Thr Leu Leu Thr Arg Leu Asp Gly Thr
                660                 665                 670

Pro Glu Leu Asp Glu His Phe Trp Ala Ile Leu Ser Ser His Gly Glu
                675                 680                 685

Arg Glu Ser Lys Leu Gly Arg Ala Thr Leu Val Asn Ile Thr Ile Leu
                690                 695                 700

Lys Asn Asp Tyr Pro His Gly Ile Ile Glu Phe Val Ser Asp Gly Leu
705                 710                 715                 720

Ser Ala Ser Ile Lys Glu Ser Lys Gly Glu Asp Ile Tyr His Ala Val
                725                 730                 735
```

-continued

Tyr Gly Val Ile Arg Thr Arg Gly Asn Phe Gly Ala Val Asn Val Ser
            740                 745                 750

Trp Met Val Ser Pro Asp Phe Thr Gln Asp Val Phe Pro Val Gln Gly
            755                 760                 765

Thr Val Cys Phe Gly Asp Gln Glu Phe Phe Lys Asn Ile Thr Val Tyr
            770                 775                 780

Ser Leu Val Asp Glu Ile Pro Glu Glu Met Glu Glu Phe Thr Ile Ile
785                 790                 795                 800

Leu Leu Asn Ala Thr Gly Gly Ala Gln Thr Gly Ile Arg Thr Thr Ala
            805                 810                 815

Ser Leu Arg Ile Leu Arg Asn Asp Asp Pro Val Tyr Phe Ala Glu Pro
            820                 825                 830

Cys Val Leu Arg Val Gln Glu Gly Glu Thr Ala Asn Phe Thr Val Leu
            835                 840                 845

Arg Asn Gly Ser Val Asp Gly Ala Cys Thr Val Gln Tyr Ala Thr Val
            850                 855                 860

Asp Gly Lys Ala Ser Gly Glu Glu Gly Asp Phe Ala Pro Val Glu Lys
865                 870                 875                 880

Gly Glu Thr Leu Val Phe Glu Val Gly Ser Arg Glu Gln Ser Ile Ser
            885                 890                 895

Val His Val Lys Asp Asp Gly Ile Pro Glu Thr Asp Glu Pro Phe Tyr
            900                 905                 910

Ile Val Leu Phe Asn Ser Thr Gly Asp Thr Val Val Tyr Glu Tyr Gly
            915                 920                 925

Val Ala Thr Val Ile Ile Glu Ala Asn Asp Asp Pro Asn Gly Val Phe
            930                 935                 940

Ser Leu Glu Pro Ile Asp Lys Ala Val Glu Glu Gly Lys Thr Asn Ala
945                 950                 955                 960

Phe Trp Ile Leu Arg His Arg Gly His Phe Gly Asn Val Ser Val Ala
            965                 970                 975

Trp Gln Leu Phe Gln Asn Ala Ser Leu Gln Pro Gly Gln Glu Phe Tyr
            980                 985                 990

Glu Thr Ser Gly Thr Val Asn Phe Thr Asp Gly Lys Glu Thr Lys Pro
            995                 1000                1005

Val Ile Leu Arg Ala Phe Pro Asp Arg Ile Pro Glu Phe Asn Glu
            1010                1015                1020

Phe Tyr Ile Leu Arg Leu Val Asn Ile Ser Gly Pro Gly Gly Gln
            1025                1030                1035

Leu Ala Glu Thr Asn Phe Gln Val Thr Val Met Ile Pro Phe Asn
            1040                1045                1050

Asp Asp Pro Phe Gly Ile Phe Ile Leu Asp Pro Glu Cys Leu Glu
            1055                1060                1065

Arg Glu Val Ala Glu Asp Val Leu Ser Glu Asp Met Ser Tyr
            1070                1075                1080

Ile Thr Ser Phe Thr Ile Leu Arg Gln Gln Gly Val Phe Gly Asp
            1085                1090                1095

Val Arg Val Gly Trp Glu Val Leu Ser Arg Glu Phe Thr Ala Gly
            1100                1105                1110

Leu Pro Pro Met Ile Asp Phe Ile Leu Leu Gly Ser Phe Pro Ser
            1115                1120                1125

Thr Val Pro Leu Gln Pro His Met Arg Arg His His Ser Gly Thr
            1130                1135                1140

Asp Val Leu Tyr Phe Ser Gly Leu Glu Gly Ala Phe Gly Thr Val

-continued

```
                1145                1150                1155

Asp Pro Lys Tyr Gln Pro Phe Arg Asn Asn Thr Ile Ala Asn Phe
    1160                1165                1170

Thr Phe Ser Ala Trp Val Met Pro Asn Ala Asn Thr Asn Gly Phe
    1175                1180                1185

Leu Ile Ala Lys Asp Asp Ser His Gly Ser Ile Tyr Tyr Gly Val
    1190                1195                1200

Lys Ile Gln Thr Asn Glu Thr His Val Thr Leu Ser Leu His Tyr
    1205                1210                1215

Lys Thr Phe Gly Ser Asn Val Thr Tyr Ile Ala Lys Ser Thr Val
    1220                1225                1230

Met Lys Tyr Leu Glu Glu Gly Val Trp Leu His Val Leu Ile Ile
    1235                1240                1245

Leu Asp Asp Gly Ile Ile Glu Phe Tyr Leu Asp Gly Lys Ala Met
    1250                1255                1260

Pro Arg Gly Ile Lys Ser Leu Lys Gly Glu Ala Ile Thr Asp Gly
    1265                1270                1275

Pro Gly Ile Leu Arg Ile Gly Ala Gly Met Asp Gly Gly Ala Arg
    1280                1285                1290

Phe Thr Gly Trp Met Gln Asp Val Arg Thr Tyr Glu Arg Lys Leu
    1295                1300                1305

Thr Pro Glu Glu Ile Tyr Glu Leu His Ala Val Pro Ala Arg Thr
    1310                1315                1320

Asp Leu His Pro Ile Ser Gly Tyr Leu Glu Phe Arg Gln Gly Glu
    1325                1330                1335

Ser Asn Lys Ser Phe Ile Val Ala Ala Arg Asp Asp Ser Glu Glu
    1340                1345                1350

Glu Gly Glu Glu Leu Phe Leu Leu Lys Leu Val Ser Val Asp Gly
    1355                1360                1365

Gly Ala Gln Ile Ser Lys Glu Asn Thr Thr Ala Arg Leu Arg Ile
    1370                1375                1380

Gln Lys Ser Asp Asn Ala Asn Gly Leu Phe Gly Phe Thr Gly Ala
    1385                1390                1395

Cys Ile Pro Glu Met Thr Glu Glu Gly Ser Thr Val Ser Cys Val
    1400                1405                1410

Val Glu Arg Thr Arg Gly Ala Leu Gly Tyr Val His Val Phe Tyr
    1415                1420                1425

Thr Ile Ser Gln Ile Glu Ser Glu Gly Ile Asn Tyr Leu Val Asp
    1430                1435                1440

Asp Phe Ala Asn Ala Ser Gly Thr Ile Thr Phe Leu Pro Trp Gln
    1445                1450                1455

Arg Ser Glu Val Leu Asn Leu Tyr Val Leu Asp Glu Asp Met Pro
    1460                1465                1470

Glu Leu Asn Glu Tyr Phe Arg Val Thr Leu Val Ser Ala Val Pro
    1475                1480                1485

Gly Asp Gly Lys Leu Gly Ser Thr Pro Ile Ser Gly Ala Ser Ile
    1490                1495                1500

Asp Pro Glu Lys Glu Thr Thr Gly Ile Thr Val Lys Ala Ser Asp
    1505                1510                1515

His Pro Tyr Gly Leu Met Gln Phe Ser Thr Gly Leu Pro Pro Gln
    1520                1525                1530

Pro Glu Asp Ser Met Ser Leu Pro Ala Ser Ser Val Pro His Ile
    1535                1540                1545
```

-continued

```
Thr Val Gln Glu Glu Asp Gly Glu Ile Arg Leu Leu Val Ile Arg
    1550            1555                1560

Ala Gln Gly Leu Leu Gly Arg Val Thr Val Gly Phe Arg Thr Val
    1565            1570                1575

Ser Leu Thr Ala Phe Ser Pro Glu Asp Tyr Gln Ser Thr Ala Gly
    1580            1585                1590

Thr Leu Glu Phe Gln Ser Gly Glu Arg Tyr Lys Tyr Ile Phe Val
    1595            1600                1605

Asn Ile Thr Asp Asn Ser Ile Pro Glu Leu Glu Lys Ser Phe Lys
    1610            1615                1620

Val Glu Leu Leu Asn Leu Asp Gly Val Ser Asp Leu Phe Arg
    1625            1630                1635

Val Asp Gly Ser Gly Ser Glu Ala Asp Thr Asp Phe Phe Leu
    1640            1645                1650

Pro Pro Val Leu Pro His Ala Ser Leu Gly Val Ala Ser Gln Ile
    1655            1660                1665

Leu Val Thr Ile Ala Ala Ser Asp His Ala His Gly Val Phe Glu
    1670            1675                1680

Phe Ser Pro Glu Ser Leu Phe Val Ser Gly Thr Glu Pro Glu Asp
    1685            1690                1695

Gly Tyr Ser Thr Val Val Leu Asn Val Thr Arg Thr Arg Gly Ala
    1700            1705                1710

Leu Ser Ala Val Thr Leu Gln Trp Lys Val Asp Ser Asp Leu Asp
    1715            1720                1725

Gly Asp Leu Ala Ile Thr Ser Gly Asn Ile Thr Phe Glu Thr Gly
    1730            1735                1740

Gln Arg Ile Ala Ser Ile Thr Val Glu Ile Leu Ser Asp Glu Glu
    1745            1750                1755

Pro Glu Leu Asp Lys Ala Leu Thr Val Ser Ile Leu Asn Val Ser
    1760            1765                1770

Ser Gly Ser Leu Gly Val Leu Thr Asn Ala Thr Leu Thr Ile Leu
    1775            1780                1785

Ala Ser Asp Asp Pro Tyr Gly Val Phe Ile Phe Pro Asn Lys Thr
    1790            1795                1800

Arg Pro Leu Ser Val Glu Glu Ala Thr Gln Asn Val Thr Leu Ser
    1805            1810                1815

Ile Ile Arg Leu Lys Gly Leu Met Gly Glu Val Ala Val Ser Tyr
    1820            1825                1830

Ala Thr Ile Asp Asp Met Glu Lys Pro Pro Tyr Phe Pro Pro Asn
    1835            1840                1845

Leu Ala Arg Ala Thr Gln Gly Gly Asp Tyr Ile Ser Ala Ser Gly
    1850            1855                1860

Leu Ala Leu Phe Arg Ala Asn Gln Thr Glu Ala Thr Ile Thr Ile
    1865            1870                1875

Ser Ile Leu Asp Asp Ala Glu Pro Glu Arg Ser Glu Ser Val Phe
    1880            1885                1890

Ile Glu Leu Phe Asn Ser Ser Leu Val Asp Lys Val Gln Asn Arg
    1895            1900                1905

Pro Ile Pro His Ser Pro Arg Leu Gly Pro Lys Val Glu Thr Val
    1910            1915                1920

Ala His Leu Val Ile Val Ala Asn Asp Asp Ala Phe Gly Thr Val
    1925            1930                1935
```

```
Gln Leu Ser Ala Thr Ser Val His Val Ala Glu Asn His Val Gly
    1940            1945                1950

Pro Ile Ile Asn Val Thr Arg Thr Gly Gly Thr Phe Ala Asp Val
    1955            1960                1965

Ser Val Lys Phe Lys Ala Val Pro Ile Thr Ala Ala Ala Gly Glu
    1970            1975                1980

Asp Tyr Ser Ile Ala Ser Ser Asp Val Val Leu Leu Glu Gly Glu
    1985            1990                1995

Thr Thr Lys Ala Val Pro Ile Tyr Ile Ile Asn Asp Ile Tyr Pro
    2000            2005                2010

Glu Leu Glu Glu Thr Phe Leu Val Gln Leu Leu Asn Glu Thr Thr
    2015            2020                2025

Gly Gly Ala Thr Leu Gly Pro Leu Arg Glu Ala Val Ile Thr Ile
    2030            2035                2040

Glu Ala Ser Asp Asp Pro Tyr Gly Leu Phe Gly Phe Gln Asn Thr
    2045            2050                2055

Lys Phe Ile Val Glu Glu Pro Glu Phe Asn Ser Val Arg Val Asn
    2060            2065                2070

Val Pro Ile Ile Arg Asn Ser Gly Thr Leu Gly Asn Val Thr Val
    2075            2080                2085

Gln Trp Val Ala Ile Ile Asn Gly Gln Phe Ala Thr Gly Asp Leu
    2090            2095                2100

Arg Val Val Ser Gly Asn Val Thr Phe Ala Pro Gly Glu Thr Ile
    2105            2110                2115

Gln Thr Leu Leu Leu Glu Val Leu Ala Asp Asp Val Pro Glu Ile
    2120            2125                2130

Glu Glu Val Val Gln Val Gln Leu Ala Ala Ala Ser Gly Gly Gly
    2135            2140                2145

Thr Ile Gly Leu Asp Arg Val Ala Asn Ile Val Ile Pro Ala Asn
    2150            2155                2160

Asp Asn Pro Tyr Gly Ser Val Ala Phe Val Gln Ser Val Phe Arg
    2165            2170                2175

Val Gln Glu Pro Leu Glu Arg Ser Ser Tyr Ala Asn Ile Thr Val
    2180            2185                2190

Arg Arg Ser Gly Gly His Phe Gly Arg Leu Leu Leu Cys Tyr Gly
    2195            2200                2205

Thr Ser Asp Ile Asp Val Val Ala Arg Ala Val Glu Glu Gly Glu
    2210            2215                2220

Asp Val Leu Ser Tyr Tyr Glu Ser Pro Thr Gln Gly Val Pro Asp
    2225            2230                2235

Pro Leu Trp Arg Thr Trp Val Asn Val Ser Ala Val Glu Glu Thr
    2240            2245                2250

Gln Tyr Thr Cys Ala Thr Leu Cys Leu Lys Glu Arg Ala Cys Ser
    2255            2260                2265

Ala Phe Ser Val Val Ser Gly Ala Glu Gly Pro Arg Cys Phe Trp
    2270            2275                2280

Met Thr Ser Trp Val Ser Gly Thr Val Asn Ser Ser Asp Phe Gln
    2285            2290                2295

Thr Tyr Lys Lys Asn Met Thr Arg Val Ala Ser Leu Phe Ser Gly
    2300            2305                2310

Gln Ala Val Ala Gly Ser Asp Tyr Glu Pro Val Thr Arg Gln Trp
    2315            2320                2325

Ala Val Ile Leu Glu Gly Asp Glu Phe Ala Asn Leu Thr Val Ser
```

-continued

|  | 2330 |  |  | 2335 |  |  | 2340 |  |  |
| --- | --- | --- | --- | --- | --- | --- | --- | --- | --- |
| Val | Leu | Pro | Asp | Asp | Ala | Pro | Glu | Met | Asp | Glu | Ser | Phe | Leu | Ile |
| 2345 |  |  |  |  | 2350 |  |  |  |  | 2355 |  |  |  |  |
| Ser | Leu | Leu | Glu | Val | His | Leu | Met | Asn | Ile | Ser | Asp | Ser | Phe | Lys |
| 2360 |  |  |  |  | 2365 |  |  |  |  | 2370 |  |  |  |  |
| Asn | Gln | Pro | Thr | Ile | Gly | His | Pro | Asn | Thr | Ser | Ala | Val | Val | Ile |
| 2375 |  |  |  |  | 2380 |  |  |  |  | 2385 |  |  |  |  |
| Gly | Leu | Asn | Gly | Asp | Ala | Phe | Gly | Val | Phe | Ile | Ile | Tyr | Ser | Val |
| 2390 |  |  |  |  | 2395 |  |  |  |  | 2400 |  |  |  |  |
| Ser | Pro | Asn | Thr | Ser | Glu | Asp | Gly | Leu | Cys | Val | Glu | Val | Gln | Glu |
| 2405 |  |  |  |  | 2410 |  |  |  |  | 2415 |  |  |  |  |
| Gln | Pro | Gln | Thr | Ser | Val | Glu | Leu | Val | Ile | Tyr | Arg | Thr | Gly | Gly |
| 2420 |  |  |  |  | 2425 |  |  |  |  | 2430 |  |  |  |  |
| Ser | Leu | Gly | Gln | Val | Met | Val | Glu | Trp | Arg | Val | Val | Gly | Gly | Thr |
| 2435 |  |  |  |  | 2440 |  |  |  |  | 2445 |  |  |  |  |
| Ala | Thr | Glu | Gly | Leu | Asp | Phe | Met | Gly | Ala | Gly | Asp | Ile | Leu | Thr |
| 2450 |  |  |  |  | 2455 |  |  |  |  | 2460 |  |  |  |  |
| Phe | Ala | Glu | Gly | Glu | Thr | Lys | Lys | Met | Ala | Ile | Leu | Thr | Ile | Leu |
| 2465 |  |  |  |  | 2470 |  |  |  |  | 2475 |  |  |  |  |
| Asp | Asp | Ser | Glu | Pro | Glu | Asp | Asn | Glu | Ser | Ile | Leu | Val | Arg | Leu |
| 2480 |  |  |  |  | 2485 |  |  |  |  | 2490 |  |  |  |  |
| Val | Ala | Thr | Glu | Gly | Gly | Ser | Arg | Ile | Leu | Pro | Ser | Ser | Asp | Thr |
| 2495 |  |  |  |  | 2500 |  |  |  |  | 2505 |  |  |  |  |
| Val | Thr | Val | Asn | Ile | Leu | Ala | Asn | Asp | Asn | Val | Ala | Gly | Ile | Val |
| 2510 |  |  |  |  | 2515 |  |  |  |  | 2520 |  |  |  |  |
| Ser | Phe | Gln | Thr | Ala | Ser | Arg | Ser | Val | Ile | Gly | His | Glu | Gly | Glu |
| 2525 |  |  |  |  | 2530 |  |  |  |  | 2535 |  |  |  |  |
| Met | Leu | Gln | Phe | His | Val | Val | Arg | Thr | Pro | Pro | Gly | Arg | Gly | Asn |
| 2540 |  |  |  |  | 2545 |  |  |  |  | 2550 |  |  |  |  |
| Val | Thr | Val | Asn | Trp | Lys | Val | Val | Gly | Gln | Asn | Leu | Glu | Val | Asn |
| 2555 |  |  |  |  | 2560 |  |  |  |  | 2565 |  |  |  |  |
| Phe | Ala | Asn | Phe | Thr | Gly | Gln | Leu | Phe | Phe | Ser | Glu | Gly | Thr | Leu |
| 2570 |  |  |  |  | 2575 |  |  |  |  | 2580 |  |  |  |  |
| Asn | Lys | Thr | Ile | Phe | Val | His | Leu | Leu | Asp | Asp | Asn | Ile | Pro | Glu |
| 2585 |  |  |  |  | 2590 |  |  |  |  | 2595 |  |  |  |  |
| Glu | Lys | Glu | Val | Tyr | Gln | Val | Val | Leu | Tyr | Asp | Val | Lys | Thr | Gln |
| 2600 |  |  |  |  | 2605 |  |  |  |  | 2610 |  |  |  |  |
| Gly | Val | Ser | Pro | Ala | Gly | Val | Ala | Leu | Leu | Asp | Ala | Gln | Gly | Tyr |
| 2615 |  |  |  |  | 2620 |  |  |  |  | 2625 |  |  |  |  |
| Ala | Ala | Val | Leu | Thr | Val | Glu | Ala | Ser | Asp | Glu | Pro | His | Gly | Val |
| 2630 |  |  |  |  | 2635 |  |  |  |  | 2640 |  |  |  |  |
| Leu | Asn | Phe | Ala | Leu | Ser | Ser | Arg | Phe | Val | Val | Leu | Gln | Glu | Ala |
| 2645 |  |  |  |  | 2650 |  |  |  |  | 2655 |  |  |  |  |
| Asn | Val | Thr | Ile | Gln | Leu | Phe | Val | Asn | Arg | Glu | Phe | Gly | Ser | Leu |
| 2660 |  |  |  |  | 2665 |  |  |  |  | 2670 |  |  |  |  |
| Gly | Ala | Ile | Asn | Val | Thr | Tyr | Ala | Thr | Val | Pro | Gly | Ile | Val | Ser |
| 2675 |  |  |  |  | 2680 |  |  |  |  | 2685 |  |  |  |  |
| Leu | Lys | Asn | Asn | Thr | Glu | Gly | Asn | Leu | Ala | Glu | Pro | Glu | Ser | Asp |
| 2690 |  |  |  |  | 2695 |  |  |  |  | 2700 |  |  |  |  |
| Phe | Ile | Pro | Val | Val | Gly | Ser | Leu | Val | Leu | Glu | Glu | Gly | Glu | Thr |
| 2705 |  |  |  |  | 2710 |  |  |  |  | 2715 |  |  |  |  |
| Thr | Ala | Ala | Ile | Ser | Ile | Thr | Val | Leu | Glu | Asp | Asp | Ile | Pro | Glu |
| 2720 |  |  |  |  | 2725 |  |  |  |  | 2730 |  |  |  |  |

```
Leu Lys Glu Tyr Phe Leu Val Asn Leu Thr His Val Asp Leu Ile
    2735                2740                2745

Met Ala Pro Leu Thr Ser Ser Pro Pro Arg Leu Gly Met Gly Leu
    2750                2755                2760

Ser Phe Met Asn Leu Leu Thr Asn Cys Glu Ser Gln Arg Thr Ser
    2765                2770                2775

Leu Phe
    2780

<210> SEQ ID NO 3
<211> LENGTH: 9018
<212> TYPE: DNA
<213> ORGANISM: Homo sapiens
<220> FEATURE:
<221> NAME/KEY: n
<222> LOCATION: (585)..(585)
<223> OTHER INFORMATION: wherein n is a, g, c, or t.

<400> SEQUENCE: 3
ctactttatt agtaaatctt ctttcagctt tactcatcct atttgtgttt ggagaaacag      60
aaataagatt tacttggaca aactgaattt gttgttaatg aaacaagtac aacagttatt     120
cgtcttatca ttgaaaggat aggagagcca gcaaatgtta ctgcaattgt atcgctgtat     180
ggagaggacg ctggtgactt ttttgacaca tatgctgcag cttttatacc tgccggagaa     240
acaaacagaa cagtgtacat agcagtatgt gatgatgact accagagcc tgacgaaact     300 tttattttc acttaacatt acagaaacct tcagcaaatg tgaagcttgg atggccaagg     360
actgttactg tgacaatatt atcaaatgac aatgcatttg gaattatttc atttaatatg     420
cttccctcaa tcgcagtgag tgagcccaag ggcagaaatg agtctatgcc tcttactctc     480
atcagggaaa agggaaccta tggaatggtc atggtgactt tgaggtaga gggtggccca     540 aatcccctg atgaagattt gagtccagtt aaaggaaata tcacnttcc ccctggcaga      600 gcaacagtaa tttataactt gacagtactc gatgacgagg taccagaaaa tgatgaaata     660
tttttaattc aactgaaaag tgtagaagga ggagctgaga ttaacacctc taggaattcc     720
attgagatca tcattaagaa aaatgatagt cccgtgagat tccttcagag tatttatttg     780
gttcctgagg aagaccacat actcataatt ccagtagttc gtggaaagga caacaatgga     840
aatctgattg gatctgatga atatgaggtt tcaatcagtt atgctgtcac aactgggaat     900
tccacagcac atgcccagca aaatctggac ttcattgatc ttcagccaaa cacaactgtt     960 gttttttccac ctttttattca tgaatctcac ttgaaatttc aaatagttga tgacaccata    1020
ccggagattc tgaatcgtt tcacattatg ttactaaaag ataccttaca gggagatgct    1080
gtgctaataa gcccttctgt tgtacaagtc accattaagc caaatgataa accttatgga    1140
gtcctttcat tcaacagtgt tttgtttgaa aggacagtta taattgatga agatagaata    1200
tcaagatatg aagaaatcac agtggttaga aatggaggaa cccatgggaa tgtctctgcg    1260
aattgggtgt tgacacggaa cagcactgat ccctcaccag taacagcaga tatcagaccg    1320
agctctggag ttctccattt tgcacaaggg cagatgttgg caacaattcc tcttactgtg    1380
gttgatgatg atcttccaga agaggcagaa gcttatctac ttcaaattct gcctcataca    1440
atacgaggag gtgcagaagt gagcgagcca gcggagcttt tgttctacat tcaggatagt    1500
gatgatgtct atggcctaat aacatttttt cctatggaaa accagaagat tgaaagcagc    1560
ccaggtgaac gatacttatc cttgagtttt acaagactag gagggactaa aggagatgtg    1620
```

```
aggttgcttt attctgtact ttacattcct gctggagctg tggaccccctt gcaagcaaaa   1680 gaaggcatct taaatatatc agggagaaat gacctcattt ttccagagca aaaaactcaa   1740
gtcactacaa aattaccaat aagaaatgat gcattccttc aaaatggagc tcactttcta   1800
gtacagttgg aaactgtgga gttgttaaac ataattcctc taatcccacc cataagcccct  1860 agatttgggg aaatctgcaa tatttctttta ctggttactc cagccattgc aaatggagaa   1920
attggctttc tcagcaatct tccaattatt ttgcatgaac tagaagattt tgctgctgaa   1980
gtggtataca ttcccttaca tcgggatgga actgatggcc aggctactgt ctactggagt   2040 ttgaagcccct ctggctttaa ttcaaaagca gtgaccccgg atgatatagg cccccttaat   2100
ggctctgttt tgtttttatc tgggcaaagt gacacaacaa tcaacattac tatcaaaggt   2160
gatgacatac cggaaatgaa tgaaactgta acactttctc tagacagggt taacgtggaa   2220
aaccaagtgc tgaaatctgg atatactagc cgtgacctaa ttattttgga aaatgatgac   2280
cctgggggag tttttgaatt ttctcctgct tccagaggac cctatgttat aaagaagga   2340 gaatctgtag agctccacat catccgatca agggggtccc ttgttaagca gtttctacac   2400
taccgagtag agccaagaga tagcaatgaa ttctatggaa acacgggagt actagaattt   2460
aaacctggag aaagggagat agtgatcacc ttgctagcaa gattggatgg gataccagag   2520
ttggatgaac actactgggt ggtcctcagc agccacggag aacgggaaag caagttggga   2580
agtgccacca ttgtcaatat aacgattctg aaaaatgatg atcctcatgg cattatagaa   2640
tttgtttctg atggtctaat tgtgatgata aatgaaagca aaggagatgc tatctatagt   2700
gctgtttatg atgtagtaag aaatcgaggc aactttggtg atgttagtgt atcatgggtg   2760
gttagtccag actttacaca agatgtattt cctgtacaag ggactgttgt ctttggagat   2820
caggaatttt caaaaaatat caccatttac tcccttccag atgagattcc agaagaaatg   2880
gaagaattta ccgttatcct actgaatggc actggaggag ctaaagtggg aaatagaaca   2940
actgcaactc tgaggattag aagaaatgat gaccccattt attttgcaga acctcgtgta   3000
gtgagggttc aggaaggtga gactgccaac tttacagttc tcagaaatgg atctgttgat   3060
gtgacttgca tggtccagta tgctaccaag gatgggaagg ctactgcaag agagagagat   3120
ttcattcctg ttgaaaaagg agaaacgctc attttgagg ttggaagtag acagcagagc   3180
atatccatat ttgttaatga agatggtatc ccggaaacag atgagcccctt ttatataatc   3240 ctcttgaatt caacaggtga tacagtagta tatcaatatg gagtagctac agtaataatt   3300
gaagctaatg atgacccaaa tggcattttt tctctggagc ccatagacaa agcagtggaa   3360
gaaggaaaga ctaatgcatt ttggattttg aggcaccgag gatactttgg tagtgtttct   3420
gtatcttggc agctctttca gaatgattct gcttttgcagc ctgggcagga gttctatgaa   3480
acttcaggaa ctgttaactt catggatgga gaagaagcaa aaccaatcat tctccatgct   3540
tttccagata aaattcctga attcaatgaa ttttattttcc taaaacttgt aaacatttca   3600
ggtggatccc caggtcctgg gggccagcta gcagaaacca acctccaggt gacagtaatg   3660
gttccattca atgatgatcc ctttggagtt tttatcttgg atccagagtg tttagagaga   3720
gaagtggcag aagatgtcct gtctgaagat gatatgtctt atattaccaa cttcaccatt   3780
ttgaggcagc agggtgtgtt tggtgatgta caactgggct gggaaatact gtccagtgag   3840
ttccctgctg gtttgccacc aatgatagat ttttttactgg ttggaattttt ccccaccacc   3900 gtgcatttac aacagcacat gcggcgtcac cacagtggaa cggatgctt gtactttacc   3960 ggactagagg gtgcatttgg gactgttaat ccaaaatacc atccctccag gaataataca   4020
```

-continued

```
attgccaact ttacattctc agcttgggta atgcccaatg ccaatacgaa tggattcatt    4080
atagcgaagg atgacggtaa tggaagcatc tactacgggg taaaaataca acaaacgaa    4140
tcccatgtga cactttccct tcattataaa accttgggtt ccaatgctac atacattgcc    4200
aagacaacag tcatgaaata tttagaagaa agtgtttggc ttcatctact aattatcctg    4260
gaggatggta taatcgaatt ctacctggat ggaaatgcaa tgcccagggg aatcaagagt    4320
ctgaaaggag aagccattac tgacggtcct gggatactga aattggagc agggataaat    4380
ggcaatgaca gatttacagg tctgatgcag gatgtgaggt cctatgagcg aaactgacg    4440
cttgaagaaa tttatgaact tcatgccatg cccgcaaaaa gtgatttaca cccaatttct    4500
ggatatctgg agttcagaca gggagaaact aacaaatcat tcattatttc tgcaagagat    4560
gacaatgacg aggaaggaga agaattattc attcttaaac tagtttctgt atatggagga    4620
gctcgtattt cggaagaaaa tactgctgca agattaacaa tacaaaaaag tgacaatgca    4680
aatggcttgt ttggtttcac aggagcttgt ataccagaga ttgcagagga gggatcaacc    4740
atttcttgtg tggttgagag aaccagagga gctctggatt atgtgcatgt tttttacacc    4800
atttcacaga ttgaaactga tggcattaat taccttgttg atgactttgc taatgccagt    4860
ggaactatta cattccttcc ttggcagaga tcagaggttc tgaatatata tgttcttgat    4920
gatgatattc ctgaacttaa tgagtatttc cgtgtgacat tggtttctgc aattcctgga    4980
gatgggaagc taggctcaac tcctaccagt ggtgcaagca tagatcctga aaaggaaacg    5040
actgatatca ccatcaaagc tagtgatcat ccatatggct tgctgcagtt ctccacaggg    5100
ctgcctcctc agcctaagga cgcaatgacc ctgcctgcaa gcagcgttcc acatatcact    5160
gtggaggagg aagatggaga aatcaggtta ttggtcatcc gtgcacaggg acttctggga    5220
agggtgactg cggaatttag aacagtgtcc ttgacagcat tcagtcctga ggattaccag    5280
aatgttgctg gcacattaga atttcaacca ggagaaagat ataaatacat tttcataaac    5340
atcactgata attctattcc tgaactggaa aaatctttta agttgagtt gttaaacttg    5400
gaaggaggag ctgaactctt tagggttgat ggaagtggta gtggtgatgg ggacatggaa    5460
ttcttccttc caactattca caaacgtgcc agtctaggag tggcttccca aattctagtg    5520
acaattgcag cctctgacca cgctcatggc gtatttgaat ttagccctga gtcactcttt    5580
gtcagtggaa ctgaaccaga agatgggtat agcactgtta cattaaatgt tataagacat    5640
catgaactc tgtctccagt gactttgcat tggaacatag actctgatcc tgatggtgat    5700
ctcgccttca ccctctggcaa catcacattt gagattgggc agacgagcgc caatatcact    5760
gtggagatat tgcctgacga agacccagaa ctggataagg cattctctgt gtcagtcctc    5820
agtgttttcca gtggttcttt gggagctcat attaatgcca cgttaacagt tttggctagt    5880
gatgatccat atgggatatt catttttcct gagaaaaaca gacctgttaa agttgaggaa    5940
gcaacccaga acatcacact atcaataata aggttgaaag gcctcatggg aaaagtcctt    6000
gtctcatatg caacactaga tgctatggaa aaaccacctt attttccacc taatttagcg    6060
agagcaactc aaggaagaga ctatatacca gcttctggat ttgctctttt tggagctaat    6120
cagagtgagg caacaatagc tatttcaatt ttggatgatg atgagccaga aaggtccgaa    6180
tctgtctttta tcgaactact caactctact ttagtagcga agtacagag tcgttcaatt    6240
ccaaattctc cacgtcttgg gcctaaggta gaaactattg cgcaactaat tatcattgcc    6300
aatgatgatg catttggaac tcttcagctc tcagcaccaa ttgtccgagt ggcagaaaat    6360
```

-continued

```
catgttggac ccattatcaa tgtgactaga acaggaggag catttgcaga tgtctctgtg    6420
aagtttaaag ctgtgccaat aactgcaata gctggtgaag attatagtat agcttcatca    6480
ggtgtggtct tgctagaagg ggaaaccagt aaagccgtgc caatatatgt cattaatgat    6540
atctatcctg aactgggaga atcttttctt gggcaactga tgaatgaaac gacaggagga    6600
gccagactag gggctttaac agaggcagtc attattattg aggcctctga tgacccctat    6660
ggattatttg ggtttcaaat tactaaactt attgtagagg aacctgagtt taactcagtg    6720
aagtaaaacc tgccaataat tcgaaattct gggacactcg gcaatgttac tgttcagtgg    6780
gttgccacca ttaatggaca gcttgctact ggcgacctgc gagttgtctc aggtaatgtg    6840
acctttgccc ctggggaaac cattcaaacc ttgttgttag aggtcctggc tgacgacgtt    6900
ccggagattg aagaggttat ccaagtgcaa ctaactgatg cctctggtgg aggtactatt    6960
gggttagatc gaattgcaaa tattattatt cctgccaatg atgatcctta tggtacagta    7020
gcctttgctc agtggtttta tcgtgttcaa gagcctctgg agagaagttc ctatgctaac    7080
ataactgtca ggcgaagcgg agggcacttt ggtcggctgt tgttgttcta cagtacttcc    7140
gacattgatg tagtggctct ggcaatggag gaaggtcaag atttactgtc ctactatgaa    7200
tctccaattc aaggggtgcc tgacccactt tggagaactt ggatgaatgt ctctgccgtg    7260
ggggagcccc tgtatacctg tgccactttg tgccttaagg aacaagcttg ctcagcgttt    7320 tcattttca gtgcttctga gggtccccag cgtttctgga tgacatcatg gatcagccca    7380
gctgtcagca attcagactt ctggacctac aggaaaaaca tgaccagggt agcatctctt    7440
tttagtggtc aggctgtggc tgggagtgac tatgagcctg tgacaaggca atgggccata    7500
atgcaggaag gtgatgaatt cgcaaatctc acagtgtcta ttcttcctga tgatttccca    7560
gagatggatg agagttttct aatttctctc cttgaagttc acctcatgaa catttcagcc    7620
agtttgaaaa atcagccaac cataggacag ccaaatattt ctacagttgt catagcacta    7680
aatggtgatg cctttggagt gtttgtgatc tacagtatta gtcccaatac ttccgaagat    7740
ggcttatttg ttgaagttca ggagcagccc caaaccttgg tggagctgat gatacacagg    7800 acaggggca gcttaggtca agtggcagtc gaatggcgtg ttgttggtgg aacagctact    7860
gaaggtttag atttttatagg tgctggagag attctgacct tgctgaagg tgaaaccaaa    7920 aagacagtca ttttaaccat cttggatgac tctgaaccag aggatgacga agtatcata    7980 gttagtttgg tgtacactga aggtggaagt agaattttgc caagctccga cactgttaga    8040
gtgaacattt tggccaatga caatgtggca ggaattgtta gctttcagac agcttccaga    8100
tctgtcatag gtcatgaagg agaaatttta caattccatg tgataagaac tttccctggt    8160
cgaggaaatg ttactgttaa ctggaaaatt attgggcaaa atctagaact caattttgct    8220
aactttagcg gacaactttt cttttcctgag gggtcgttga atacaacatt gtttgtgcat    8280
ttgttggatg acaacattcc tgaggagaaa gaagtatacc aagtcattct gtatgatgtc    8340
aggacacaag gagttccacc agccggaatc gccctgcttg atactcaagg atatgccgct    8400
gtcctcacag tagaagccag tgatgaacca catggagttt taaattttgc tctttcatca    8460
agatttgtgt tactacaaga ggctaacata acaattcagc ttttcatcaa cagagaattt    8520
ggatctctcg gagctatcaa tgtcacatat accacggttc ctggaatgct gagtctgaag    8580
aaccaaacag taggaaacct agcagagcca gaagttgatt tgtccctat cattggcttt    8640 ctgattttag aagaaggga aacagcagca gccatcaaca ttaccattct tgaggatgat    8700
gtaccagagc tagaagaata tttcctggtg aatttaactt acgttggact taccatggct    8760
```

-continued

```
gcttcaactt catttcctcc cagactaggt atgaggggtt tcttgtttgt ttctttttgc     8820
tcacttcaaa tgaaatgaag aaacttcatt tttgaatcag aagtgatcat tgtgctgttt     8880
tgttaatctt agctatgtgt taaaatatga tgggctttta tatttatttt tgatactctc     8940
atatattgca attttttacaa tgaacaatgt aaagacatta aaaattattg tgtgatgctc    9000
tttaaatttt acaactat                                                   9018
```

<210> SEQ ID NO 4
<211> LENGTH: 2777
<212> TYPE: PRT
<213> ORGANISM: Homo sapiens

<400> SEQUENCE: 4

```
Met Val Met Val Thr Phe Glu Val Glu Gly Gly Pro Asn Pro Pro Asp
  1               5                  10                  15

Glu Asp Leu Ser Pro Val Lys Gly Asn Ile Thr Phe Pro Pro Gly Arg
             20                  25                  30

Ala Thr Val Ile Tyr Asn Leu Thr Val Leu Asp Asp Glu Val Pro Glu
         35                  40                  45

Asn Asp Glu Ile Phe Leu Ile Gln Leu Lys Ser Val Glu Gly Gly Ala
     50                  55                  60

Glu Ile Asn Thr Ser Arg Asn Ser Ile Glu Ile Ile Lys Lys Asn
 65                  70                  75                  80

Asp Ser Pro Val Arg Phe Leu Gln Ser Ile Tyr Leu Val Pro Glu Glu
             85                  90                  95

Asp His Ile Leu Ile Pro Val Val Arg Gly Lys Asp Asn Asn Gly
            100                 105                 110

Asn Leu Ile Gly Ser Asp Glu Tyr Glu Val Ser Ile Ser Tyr Ala Val
            115                 120                 125

Thr Thr Gly Asn Ser Thr Ala His Ala Gln Gln Asn Leu Asp Phe Ile
        130                 135                 140

Asp Leu Gln Pro Asn Thr Thr Val Val Phe Pro Pro Phe Ile His Glu
145                 150                 155                 160

Ser His Leu Lys Phe Gln Ile Val Asp Asp Thr Ile Pro Glu Ile Ala
                165                 170                 175

Glu Ser Phe His Ile Met Leu Leu Lys Asp Thr Leu Gln Gly Asp Ala
            180                 185                 190

Val Leu Ile Ser Pro Ser Val Val Gln Val Thr Ile Lys Pro Asn Asp
        195                 200                 205

Lys Pro Tyr Gly Val Leu Ser Phe Asn Ser Val Leu Phe Glu Arg Thr
    210                 215                 220

Val Ile Ile Asp Glu Asp Arg Ile Ser Arg Tyr Glu Glu Ile Thr Val
225                 230                 235                 240

Val Arg Asn Gly Gly Thr His Gly Asn Val Ser Ala Asn Trp Val Leu
                245                 250                 255

Thr Arg Asn Ser Thr Asp Pro Ser Pro Val Thr Ala Asp Ile Arg Pro
            260                 265                 270

Ser Ser Gly Val Leu His Phe Ala Gln Gly Gln Met Leu Ala Thr Ile
        275                 280                 285

Pro Leu Thr Val Val Asp Asp Asp Leu Pro Glu Glu Ala Glu Ala Tyr
    290                 295                 300

Leu Leu Gln Ile Leu Pro His Thr Ile Arg Gly Gly Ala Glu Val Ser
305                 310                 315                 320
```

```
Glu Pro Ala Glu Leu Leu Phe Tyr Ile Gln Asp Ser Asp Val Tyr
            325                 330                 335

Gly Leu Ile Thr Phe Phe Pro Met Glu Asn Gln Lys Ile Glu Ser Ser
                340                 345                 350

Pro Gly Glu Arg Tyr Leu Ser Leu Ser Phe Thr Arg Leu Gly Gly Thr
            355                 360                 365

Lys Gly Asp Val Arg Leu Leu Tyr Ser Val Leu Tyr Ile Pro Ala Gly
    370                 375                 380

Ala Val Asp Pro Leu Gln Ala Lys Glu Gly Ile Leu Asn Ile Ser Gly
385                 390                 395                 400

Arg Asn Asp Leu Ile Phe Pro Glu Gln Lys Thr Gln Val Thr Thr Lys
                405                 410                 415

Leu Pro Ile Arg Asn Asp Ala Phe Leu Gln Asn Gly Ala His Phe Leu
            420                 425                 430

Val Gln Leu Glu Thr Val Glu Leu Leu Asn Ile Ile Pro Leu Ile Pro
        435                 440                 445

Pro Ile Ser Pro Arg Phe Gly Glu Ile Cys Asn Ile Ser Leu Leu Val
    450                 455                 460

Thr Pro Ala Ile Ala Asn Gly Glu Ile Gly Phe Leu Ser Asn Leu Pro
465                 470                 475                 480

Ile Ile Leu His Glu Leu Glu Asp Phe Ala Ala Glu Val Val Tyr Ile
                485                 490                 495

Pro Leu His Arg Asp Gly Thr Asp Gly Gln Ala Thr Val Tyr Trp Ser
            500                 505                 510

Leu Lys Pro Ser Gly Phe Asn Ser Lys Ala Val Thr Pro Asp Asp Ile
    515                 520                 525

Gly Pro Phe Asn Gly Ser Val Leu Phe Leu Ser Gly Gln Ser Asp Thr
530                 535                 540

Thr Ile Asn Ile Thr Ile Lys Gly Asp Asp Ile Pro Glu Met Asn Glu
545                 550                 555                 560

Thr Val Thr Leu Ser Leu Asp Arg Val Asn Val Glu Asn Gln Val Leu
                565                 570                 575

Lys Ser Gly Tyr Thr Ser Arg Asp Leu Ile Ile Leu Glu Asn Asp Asp
            580                 585                 590

Pro Gly Gly Val Phe Glu Phe Ser Pro Ala Ser Arg Gly Pro Tyr Val
    595                 600                 605

Ile Lys Glu Gly Glu Ser Val Glu Leu His Ile Ile Arg Ser Arg Gly
610                 615                 620

Ser Leu Val Lys Gln Phe Leu His Tyr Arg Val Glu Pro Arg Asp Ser
625                 630                 635                 640

Asn Glu Phe Tyr Gly Asn Thr Gly Val Leu Glu Phe Lys Pro Gly Glu
                645                 650                 655

Arg Glu Ile Val Ile Thr Leu Leu Ala Arg Leu Asp Gly Ile Pro Glu
            660                 665                 670

Leu Asp Glu His Tyr Trp Val Val Leu Ser Ser His Gly Glu Arg Glu
        675                 680                 685

Ser Lys Leu Gly Ser Ala Thr Ile Val Asn Ile Thr Ile Leu Lys Asn
    690                 695                 700

Asp Asp Pro His Gly Ile Ile Glu Phe Val Ser Asp Gly Leu Ile Val
705                 710                 715                 720

Met Ile Asn Glu Ser Lys Gly Asp Ala Ile Tyr Ser Ala Val Tyr Asp
                725                 730                 735

Val Val Arg Asn Arg Gly Asn Phe Gly Asp Val Ser Val Ser Trp Val
```

-continued

```
                   740                 745                 750
Val Ser Pro Asp Phe Thr Gln Asp Val Phe Pro Val Gln Gly Thr Val
                755                 760                 765
Val Phe Gly Asp Gln Glu Phe Ser Lys Asn Ile Thr Ile Tyr Ser Leu
            770                 775                 780
Pro Asp Glu Ile Pro Glu Glu Met Glu Glu Phe Thr Val Ile Leu Leu
785                 790                 795                 800
Asn Gly Thr Gly Gly Ala Lys Val Gly Asn Arg Thr Ala Thr Leu
                    805                 810                 815
Arg Ile Arg Arg Asn Asp Asp Pro Ile Tyr Phe Ala Glu Pro Arg Val
                820                 825                 830
Val Arg Val Gln Glu Gly Glu Thr Ala Asn Phe Thr Val Leu Arg Asn
                835                 840                 845
Gly Ser Val Asp Val Thr Cys Met Val Gln Tyr Ala Thr Lys Asp Gly
            850                 855                 860
Lys Ala Thr Ala Arg Glu Arg Asp Phe Ile Pro Val Glu Lys Gly Glu
865                 870                 875                 880
Thr Leu Ile Phe Glu Val Gly Ser Arg Gln Gln Ser Ile Ser Ile Phe
                        885                 890                 895
Val Asn Glu Asp Gly Ile Pro Glu Thr Asp Glu Pro Phe Tyr Ile Ile
                900                 905                 910
Leu Leu Asn Ser Thr Gly Asp Thr Val Val Tyr Gln Tyr Gly Val Ala
            915                 920                 925
Thr Val Ile Ile Glu Ala Asn Asp Asp Pro Asn Gly Ile Phe Ser Leu
            930                 935                 940
Glu Pro Ile Asp Lys Ala Val Glu Glu Gly Lys Thr Asn Ala Phe Trp
945                 950                 955                 960
Ile Leu Arg His Arg Gly Tyr Phe Gly Ser Val Ser Val Ser Trp Gln
                965                 970                 975
Leu Phe Gln Asn Asp Ser Ala Leu Gln Pro Gly Gln Glu Phe Tyr Glu
                980                 985                 990
Thr Ser Gly Thr Val Asn Phe Met  Asp Gly Glu Glu Ala  Lys Pro Ile
            995                 1000                1005
Ile Leu  His Ala Phe Pro Asp  Lys Ile Pro Glu Phe  Asn Glu Phe
    1010                1015                1020
Tyr Phe  Leu Lys Leu Val Asn  Ile Ser Gly Gly Ser  Pro Gly Pro
    1025                1030                1035
Gly Gly  Gln Leu Ala Glu Thr  Asn Leu Gln Val Thr  Val Met Val
    1040                1045                1050
Pro Phe  Asn Asp Asp Pro Phe  Gly Val Phe Ile Leu  Asp Pro Glu
    1055                1060                1065
Cys Leu  Glu Arg Glu Val Ala  Glu Asp Val Leu Ser  Glu Asp Asp
    1070                1075                1080
Met Ser  Tyr Ile Thr Asn Phe  Thr Ile Leu Arg Gln  Gln Gly Val
    1085                1090                1095
Phe Gly  Asp Val Gln Leu Gly  Trp Glu Ile Leu Ser  Ser Glu Phe
    1100                1105                1110
Pro Ala  Gly Leu Pro Pro Met  Ile Asp Phe Leu Leu  Val Gly Ile
    1115                1120                1125
Phe Pro  Thr Thr Val His Leu  Gln Gln His Met Arg  Arg His His
    1130                1135                1140
Ser Gly  Thr Asp Ala Leu Tyr  Phe Thr Gly Leu Glu  Gly Ala Phe
    1145                1150                1155
```

-continued

| | | | | | | | | | | |
|---|---|---|---|---|---|---|---|---|---|---|
| Gly | Thr | Val | Asn | Pro | Lys | Tyr | His | Pro | Ser | Arg | Asn | Asn | Thr | Ile |
| | 1160 | | | | 1165 | | | | 1170 | |
| Ala | Asn | Phe | Thr | Phe | Ser | Ala | Trp | Val | Met | Pro | Asn | Ala | Asn | Thr |
| | 1175 | | | | 1180 | | | | 1185 | |
| Asn | Gly | Phe | Ile | Ile | Ala | Lys | Asp | Asp | Gly | Asn | Gly | Ser | Ile | Tyr |
| | 1190 | | | | 1195 | | | | 1200 | |
| Tyr | Gly | Val | Lys | Ile | Gln | Thr | Asn | Glu | Ser | His | Val | Thr | Leu | Ser |
| | 1205 | | | | 1210 | | | | 1215 | |
| Leu | His | Tyr | Lys | Thr | Leu | Gly | Ser | Asn | Ala | Thr | Tyr | Ile | Ala | Lys |
| | 1220 | | | | 1225 | | | | 1230 | |
| Thr | Thr | Val | Met | Lys | Tyr | Leu | Glu | Glu | Ser | Val | Trp | Leu | His | Leu |
| | 1235 | | | | 1240 | | | | 1245 | |
| Leu | Ile | Ile | Leu | Glu | Asp | Gly | Ile | Ile | Glu | Phe | Tyr | Leu | Asp | Gly |
| | 1250 | | | | 1255 | | | | 1260 | |
| Asn | Ala | Met | Pro | Arg | Gly | Ile | Lys | Ser | Leu | Lys | Gly | Glu | Ala | Ile |
| | 1265 | | | | 1270 | | | | 1275 | |
| Thr | Asp | Gly | Pro | Gly | Ile | Leu | Arg | Ile | Gly | Ala | Gly | Ile | Asn | Gly |
| | 1280 | | | | 1285 | | | | 1290 | |
| Asn | Asp | Arg | Phe | Thr | Gly | Leu | Met | Gln | Asp | Val | Arg | Ser | Tyr | Glu |
| | 1295 | | | | 1300 | | | | 1305 | |
| Arg | Lys | Leu | Thr | Leu | Glu | Glu | Ile | Tyr | Glu | Leu | His | Ala | Met | Pro |
| | 1310 | | | | 1315 | | | | 1320 | |
| Ala | Lys | Ser | Asp | Leu | His | Pro | Ile | Ser | Gly | Tyr | Leu | Glu | Phe | Arg |
| | 1325 | | | | 1330 | | | | 1335 | |
| Gln | Gly | Glu | Thr | Asn | Lys | Ser | Phe | Ile | Ile | Ser | Ala | Arg | Asp | Asp |
| | 1340 | | | | 1345 | | | | 1350 | |
| Asn | Asp | Glu | Glu | Gly | Glu | Glu | Leu | Phe | Ile | Leu | Lys | Leu | Val | Ser |
| | 1355 | | | | 1360 | | | | 1365 | |
| Val | Tyr | Gly | Gly | Ala | Arg | Ile | Ser | Glu | Glu | Asn | Thr | Ala | Ala | Arg |
| | 1370 | | | | 1375 | | | | 1380 | |
| Leu | Thr | Ile | Gln | Lys | Ser | Asp | Asn | Ala | Asn | Gly | Leu | Phe | Gly | Phe |
| | 1385 | | | | 1390 | | | | 1395 | |
| Thr | Gly | Ala | Cys | Ile | Pro | Glu | Ile | Ala | Glu | Glu | Gly | Ser | Thr | Ile |
| | 1400 | | | | 1405 | | | | 1410 | |
| Ser | Cys | Val | Val | Glu | Arg | Thr | Arg | Gly | Ala | Leu | Asp | Tyr | Val | His |
| | 1415 | | | | 1420 | | | | 1425 | |
| Val | Phe | Tyr | Thr | Ile | Ser | Gln | Ile | Glu | Thr | Asp | Gly | Ile | Asn | Tyr |
| | 1430 | | | | 1435 | | | | 1440 | |
| Leu | Val | Asp | Asp | Phe | Ala | Asn | Ala | Ser | Gly | Thr | Ile | Thr | Phe | Leu |
| | 1445 | | | | 1450 | | | | 1455 | |
| Pro | Trp | Gln | Arg | Ser | Glu | Val | Leu | Asn | Ile | Tyr | Val | Leu | Asp | Asp |
| | 1460 | | | | 1465 | | | | 1470 | |
| Asp | Ile | Pro | Glu | Leu | Asn | Glu | Tyr | Phe | Arg | Val | Thr | Leu | Val | Ser |
| | 1475 | | | | 1480 | | | | 1485 | |
| Ala | Ile | Pro | Gly | Asp | Gly | Lys | Leu | Gly | Ser | Thr | Pro | Thr | Ser | Gly |
| | 1490 | | | | 1495 | | | | 1500 | |
| Ala | Ser | Ile | Asp | Pro | Glu | Lys | Glu | Thr | Thr | Asp | Ile | Thr | Ile | Lys |
| | 1505 | | | | 1510 | | | | 1515 | |
| Ala | Ser | Asp | His | Pro | Tyr | Gly | Leu | Leu | Gln | Phe | Ser | Thr | Gly | Leu |
| | 1520 | | | | 1525 | | | | 1530 | |
| Pro | Pro | Gln | Pro | Lys | Asp | Ala | Met | Thr | Leu | Pro | Ala | Ser | Ser | Val |
| | 1535 | | | | 1540 | | | | 1545 | |

-continued

```
Pro His Ile Thr Val Glu Glu Asp Gly Glu Ile Arg Leu Leu
1550                1555                1560

Val Ile Arg Ala Gln Gly Leu Leu Gly Arg Val Thr Ala Glu Phe
1565                1570                1575

Arg Thr Val Ser Leu Thr Ala Phe Ser Pro Glu Asp Tyr Gln Asn
1580                1585                1590

Val Ala Gly Thr Leu Glu Phe Gln Pro Gly Glu Arg Tyr Lys Tyr
1595                1600                1605

Ile Phe Ile Asn Ile Thr Asp Asn Ser Ile Pro Glu Leu Glu Lys
1610                1615                1620

Ser Phe Lys Val Glu Leu Leu Asn Leu Glu Gly Gly Ala Glu Leu
1625                1630                1635

Phe Arg Val Asp Gly Ser Gly Ser Gly Asp Gly Asp Met Glu Phe
1640                1645                1650

Phe Leu Pro Thr Ile His Lys Arg Ala Ser Leu Gly Val Ala Ser
1655                1660                1665

Gln Ile Leu Val Thr Ile Ala Ala Ser Asp His Ala His Gly Val
1670                1675                1680

Phe Glu Phe Ser Pro Glu Ser Leu Phe Val Ser Gly Thr Glu Pro
1685                1690                1695

Glu Asp Gly Tyr Ser Thr Val Thr Leu Asn Val Ile Arg His His
1700                1705                1710

Gly Thr Leu Ser Pro Val Thr Leu His Trp Asn Ile Asp Ser Asp
1715                1720                1725

Pro Asp Gly Asp Leu Ala Phe Thr Ser Gly Asn Ile Thr Phe Glu
1730                1735                1740

Ile Gly Gln Thr Ser Ala Asn Ile Thr Val Glu Ile Leu Pro Asp
1745                1750                1755

Glu Asp Pro Glu Leu Asp Lys Ala Phe Ser Val Ser Val Leu Ser
1760                1765                1770

Val Ser Ser Gly Ser Leu Gly Ala His Ile Asn Ala Thr Leu Thr
1775                1780                1785

Val Leu Ala Ser Asp Asp Pro Tyr Gly Ile Phe Ile Phe Pro Glu
1790                1795                1800

Lys Asn Arg Pro Val Lys Val Glu Glu Ala Thr Gln Asn Ile Thr
1805                1810                1815

Leu Ser Ile Ile Arg Leu Lys Gly Leu Met Gly Lys Val Leu Val
1820                1825                1830

Ser Tyr Ala Thr Leu Asp Ala Met Glu Lys Pro Pro Tyr Phe Pro
1835                1840                1845

Pro Asn Leu Ala Arg Ala Thr Gln Gly Arg Asp Tyr Ile Pro Ala
1850                1855                1860

Ser Gly Phe Ala Leu Phe Gly Ala Asn Gln Ser Glu Ala Thr Ile
1865                1870                1875

Ala Ile Ser Ile Leu Asp Asp Asp Glu Pro Glu Arg Ser Glu Ser
1880                1885                1890

Val Phe Ile Glu Leu Leu Asn Ser Thr Leu Val Ala Lys Val Gln
1895                1900                1905

Ser Arg Ser Ile Pro Asn Ser Pro Arg Leu Gly Pro Lys Val Glu
1910                1915                1920

Thr Ile Ala Gln Leu Ile Ile Ile Ala Asn Asp Asp Ala Phe Gly
1925                1930                1935

Thr Leu Gln Leu Ser Ala Pro Ile Val Arg Val Ala Glu Asn His
```

-continued

```
            1940                1945                1950
Val Gly Pro Ile Ile Asn Val Thr Arg Thr Gly Gly Ala Phe Ala
    1955                1960                1965
Asp Val Ser Val Lys Phe Lys Ala Val Pro Ile Thr Ala Ile Ala
    1970                1975                1980
Gly Glu Asp Tyr Ser Ile Ala Ser Ser Gly Val Val Leu Leu Glu
    1985                1990                1995
Gly Glu Thr Ser Lys Ala Val Pro Ile Tyr Val Ile Asn Asp Ile
    2000                2005                2010
Tyr Pro Glu Leu Gly Glu Ser Phe Leu Gly Gln Leu Met Asn Glu
    2015                2020                2025
Thr Thr Gly Gly Ala Arg Leu Gly Ala Leu Thr Glu Ala Val Ile
    2030                2035                2040
Ile Ile Glu Ala Ser Asp Asp Pro Tyr Gly Leu Phe Gly Phe Gln
    2045                2050                2055
Ile Thr Lys Leu Ile Val Glu Glu Pro Glu Phe Asn Ser Val Lys
    2060                2065                2070
Val Asn Leu Pro Ile Ile Arg Asn Ser Gly Thr Leu Gly Asn Val
    2075                2080                2085
Thr Val Gln Trp Val Ala Thr Ile Asn Gly Gln Leu Ala Thr Gly
    2090                2095                2100
Asp Leu Arg Val Val Ser Gly Asn Val Thr Phe Ala Pro Gly Glu
    2105                2110                2115
Thr Ile Gln Thr Leu Leu Leu Glu Val Leu Ala Asp Asp Val Pro
    2120                2125                2130
Glu Ile Glu Glu Val Ile Gln Val Gln Leu Thr Asp Ala Ser Gly
    2135                2140                2145
Gly Gly Thr Ile Gly Leu Asp Arg Ile Ala Asn Ile Ile Ile Pro
    2150                2155                2160
Ala Asn Asp Asp Pro Tyr Gly Thr Val Ala Phe Ala Gln Val Val
    2165                2170                2175
Tyr Arg Val Gln Glu Pro Leu Glu Arg Ser Ser Tyr Ala Asn Ile
    2180                2185                2190
Thr Val Arg Arg Ser Gly Gly His Phe Gly Arg Leu Leu Leu Phe
    2195                2200                2205
Tyr Ser Thr Ser Asp Ile Asp Val Val Ala Leu Ala Met Glu Glu
    2210                2215                2220
Gly Gln Asp Leu Leu Ser Tyr Tyr Glu Ser Pro Ile Gln Gly Val
    2225                2230                2235
Pro Asp Pro Leu Trp Arg Thr Trp Met Asn Val Ser Ala Val Gly
    2240                2245                2250
Glu Pro Leu Tyr Thr Cys Ala Thr Leu Cys Leu Lys Glu Gln Ala
    2255                2260                2265
Cys Ser Ala Phe Ser Phe Phe Ser Ala Ser Glu Gly Pro Gln Arg
    2270                2275                2280
Phe Trp Met Thr Ser Trp Ile Ser Pro Ala Val Ser Asn Ser Asp
    2285                2290                2295
Phe Trp Thr Tyr Arg Lys Asn Met Thr Arg Val Ala Ser Leu Phe
    2300                2305                2310
Ser Gly Gln Ala Val Ala Gly Ser Asp Tyr Glu Pro Val Thr Arg
    2315                2320                2325
Gln Trp Ala Ile Met Gln Glu Gly Asp Glu Phe Ala Asn Leu Thr
    2330                2335                2340
```

-continued

| | | | | | | | | | | | |
|---|---|---|---|---|---|---|---|---|---|---|---|
| Val | Ser | Ile | Leu | Pro | Asp | Asp | Phe | Pro | Glu | Met | Asp | Glu | Ser | Phe |
| 2345 | | | | 2350 | | | | 2355 | | | |

Val Ser Ile Leu Pro Asp Asp Phe Pro Glu Met Asp Glu Ser Phe
2345                2350                2355

Leu Ile Ser Leu Leu Glu Val His Leu Met Asn Ile Ser Ala Ser
2360                2365                2370

Leu Lys Asn Gln Pro Thr Ile Gly Gln Pro Asn Ile Ser Thr Val
2375                2380                2385

Val Ile Ala Leu Asn Gly Asp Ala Phe Gly Val Phe Val Ile Tyr
2390                2395                2400

Ser Ile Ser Pro Asn Thr Ser Glu Asp Gly Leu Phe Val Glu Val
2405                2410                2415

Gln Glu Gln Pro Gln Thr Leu Val Glu Leu Met Ile His Arg Thr
2420                2425                2430

Gly Gly Ser Leu Gly Gln Val Ala Val Glu Trp Arg Val Val Gly
2435                2440                2445

Gly Thr Ala Thr Glu Gly Leu Asp Phe Ile Gly Ala Gly Glu Ile
2450                2455                2460

Leu Thr Phe Ala Glu Gly Glu Thr Lys Lys Thr Val Ile Leu Thr
2465                2470                2475

Ile Leu Asp Asp Ser Glu Pro Glu Asp Asp Glu Ser Ile Ile Val
2480                2485                2490

Ser Leu Val Tyr Thr Glu Gly Gly Ser Arg Ile Leu Pro Ser Ser
2495                2500                2505

Asp Thr Val Arg Val Asn Ile Leu Ala Asn Asp Asn Val Ala Gly
2510                2515                2520

Ile Val Ser Phe Gln Thr Ala Ser Arg Ser Val Ile Gly His Glu
2525                2530                2535

Gly Glu Ile Leu Gln Phe His Val Ile Arg Thr Phe Pro Gly Arg
2540                2545                2550

Gly Asn Val Thr Val Asn Trp Lys Ile Ile Gly Gln Asn Leu Glu
2555                2560                2565

Leu Asn Phe Ala Asn Phe Ser Gly Gln Leu Phe Phe Pro Glu Gly
2570                2575                2580

Ser Leu Asn Thr Thr Leu Phe Val His Leu Leu Asp Asp Asn Ile
2585                2590                2595

Pro Glu Glu Lys Glu Val Tyr Gln Val Ile Leu Tyr Asp Val Arg
2600                2605                2610

Thr Gln Gly Val Pro Pro Ala Gly Ile Ala Leu Leu Asp Thr Gln
2615                2620                2625

Gly Tyr Ala Ala Val Leu Thr Val Glu Ala Ser Asp Glu Pro His
2630                2635                2640

Gly Val Leu Asn Phe Ala Leu Ser Ser Arg Phe Val Leu Leu Gln
2645                2650                2655

Glu Ala Asn Ile Thr Ile Gln Leu Phe Ile Asn Arg Glu Phe Gly
2660                2665                2670

Ser Leu Gly Ala Ile Asn Val Thr Tyr Thr Thr Val Pro Gly Met
2675                2680                2685

Leu Ser Leu Lys Asn Gln Thr Val Gly Asn Leu Ala Glu Pro Glu
2690                2695                2700

Val Asp Phe Val Pro Ile Ile Gly Phe Leu Ile Leu Glu Glu Gly
2705                2710                2715

Glu Thr Ala Ala Ala Ile Asn Ile Thr Ile Leu Glu Asp Asp Val
2720                2725                2730

```
Pro Glu Leu Glu Glu Tyr Phe Leu Val Asn Leu Thr Tyr Val Gly
    2735                2740                2745

Leu Thr Met Ala Ala Ser Thr Ser Phe Pro Pro Arg Leu Gly Met
    2750                2755                2760

Arg Gly Phe Leu Phe Val Ser Phe Cys Ser Leu Gln Met Lys
    2765                2770                2775

<210> SEQ ID NO 5
<211> LENGTH: 35
<212> TYPE: PRT
<213> ORGANISM: Mus musculus

<400> SEQUENCE: 5

Gly Asn Ile Thr Phe Pro Pro Gly Arg Ala Thr Val Ile Tyr Asn Val
1               5                   10                  15

Thr Val Leu Asp Asp Glu Val Pro Glu Asn Asp Glu Leu Phe Leu Ile
            20                  25                  30

Gln Leu Arg
        35

<210> SEQ ID NO 6
<211> LENGTH: 35
<212> TYPE: PRT
<213> ORGANISM: Mus musculus

<400> SEQUENCE: 6

Thr Thr Leu Val Phe Pro Pro Phe Val His Glu Ser His Leu Lys Phe
1               5                   10                  15

Gln Ile Ile Asp Asp Leu Ile Pro Glu Ile Ala Glu Ser Phe His Ile
            20                  25                  30

Met Leu Leu
        35

<210> SEQ ID NO 7
<211> LENGTH: 35
<212> TYPE: PRT
<213> ORGANISM: Mus musculus

<400> SEQUENCE: 7

Gly Thr Leu Gln Phe Ala Gln Gly Gln Met Leu Ala Pro Ile Ser Leu
1               5                   10                  15

Val Val Phe Asp Asp Asp Leu Pro Glu Glu Ala Glu Ala Tyr Leu Leu
            20                  25                  30

Thr Ile Leu
        35

<210> SEQ ID NO 8
<211> LENGTH: 35
<212> TYPE: PRT
<213> ORGANISM: Mus musculus

<400> SEQUENCE: 8

Gly Ser Val Val Phe Leu Ser Gly Gln Asn Glu Thr Ser Ile Asn Ile
1               5                   10                  15

Thr Val Lys Gly Asp Asp Ile Pro Glu Leu Asn Glu Thr Val Thr Leu
            20                  25                  30

Ser Leu Asp
        35

<210> SEQ ID NO 9
```

```
<211> LENGTH: 35
<212> TYPE: PRT
<213> ORGANISM: Mus musculus

<400> SEQUENCE: 9

Gly Val Leu Glu Phe Thr Pro Gly Glu Arg Glu Val Ile Thr Leu
1               5                   10                  15

Leu Thr Arg Leu Asp Gly Thr Pro Glu Leu Asp Glu His Phe Trp Ala
            20                  25                  30

Ile Leu Ser
        35

<210> SEQ ID NO 10
<211> LENGTH: 35
<212> TYPE: PRT
<213> ORGANISM: Mus musculus

<400> SEQUENCE: 10

Gly Thr Val Cys Phe Gly Asp Gln Glu Phe Phe Lys Asn Ile Thr Val
1               5                   10                  15

Tyr Ser Leu Val Asp Glu Ile Pro Glu Glu Met Glu Glu Phe Thr Ile
            20                  25                  30

Ile Leu Leu
        35

<210> SEQ ID NO 11
<211> LENGTH: 35
<212> TYPE: PRT
<213> ORGANISM: Mus musculus

<400> SEQUENCE: 11

Glu Thr Leu Val Phe Glu Val Gly Ser Arg Glu Gln Ser Ile Ser Val
1               5                   10                  15

His Val Lys Asp Asp Gly Ile Pro Glu Thr Asp Glu Pro Phe Tyr Ile
            20                  25                  30

Val Leu Phe
        35

<210> SEQ ID NO 12
<211> LENGTH: 35
<212> TYPE: PRT
<213> ORGANISM: Mus musculus

<400> SEQUENCE: 12

Gly Thr Val Asn Phe Thr Asp Gly Glu Glu Thr Lys Pro Val Ile Leu
1               5                   10                  15

Arg Ala Phe Pro Asp Arg Ile Pro Glu Phe Asn Glu Phe Tyr Ile Leu
            20                  25                  30

Arg Leu Val
        35

<210> SEQ ID NO 13
<211> LENGTH: 35
<212> TYPE: PRT
<213> ORGANISM: Mus musculus

<400> SEQUENCE: 13

Gly Thr Ile Thr Phe Leu Pro Trp Gln Arg Ser Glu Val Leu Asn Leu
1               5                   10                  15

Tyr Val Leu Asp Glu Asp Met Pro Glu Leu Asn Glu Tyr Phe Arg Val
            20                  25                  30
```

-continued

```
Thr Leu Val
        35

<210> SEQ ID NO 14
<211> LENGTH: 35
<212> TYPE: PRT
<213> ORGANISM: Mus musculus

<400> SEQUENCE: 14

Gly Thr Leu Glu Phe Gln Ser Gly Glu Arg Tyr Lys Tyr Ile Phe Val
1               5                   10                  15

Asn Ile Thr Asp Asn Ser Ile Pro Glu Leu Glu Lys Ser Phe Lys Val
            20                  25                  30

Glu Leu Leu
        35

<210> SEQ ID NO 15
<211> LENGTH: 35
<212> TYPE: PRT
<213> ORGANISM: Mus musculus

<400> SEQUENCE: 15

Gly Asn Ile Thr Phe Glu Thr Gly Gln Arg Ile Ala Ser Ile Thr Val
1               5                   10                  15

Glu Ile Leu Pro Asp Glu Glu Pro Glu Leu Asp Lys Ala Leu Thr Val
            20                  25                  30

Ser Ile Leu
        35

<210> SEQ ID NO 16
<211> LENGTH: 35
<212> TYPE: PRT
<213> ORGANISM: Mus musculus

<400> SEQUENCE: 16

Gly Leu Ala Leu Phe Arg Ala Asn Gln Thr Glu Ala Thr Ile Thr Ile
1               5                   10                  15

Ser Ile Leu Asp Asp Ala Glu Pro Glu Arg Ser Glu Ser Val Phe Ile
            20                  25                  30

Glu Leu Phe
        35

<210> SEQ ID NO 17
<211> LENGTH: 35
<212> TYPE: PRT
<213> ORGANISM: Mus musculus

<400> SEQUENCE: 17

Ser Asp Val Val Leu Leu Glu Gly Glu Thr Thr Lys Ala Val Pro Ile
1               5                   10                  15

Tyr Ile Ile Asn Asp Ile Tyr Pro Glu Leu Glu Glu Thr Phe Leu Val
            20                  25                  30

Gln Leu Leu
        35

<210> SEQ ID NO 18
<211> LENGTH: 35
<212> TYPE: PRT
<213> ORGANISM: Mus musculus

<400> SEQUENCE: 18
```

```
Gly Asn Val Thr Phe Ala Pro Gly Glu Thr Ile Gln Thr Leu Leu Leu
1               5                   10                  15

Glu Val Leu Ala Asp Asp Val Pro Glu Ile Glu Glu Val Val Gln Val
                20                  25                  30

Gln Leu Ala
        35
```

<210> SEQ ID NO 19
<211> LENGTH: 35
<212> TYPE: PRT
<213> ORGANISM: Mus musculus

<400> SEQUENCE: 19

```
Gln Trp Ala Val Ile Leu Glu Gly Asp Glu Phe Ala Asn Leu Thr Val
1               5                   10                  15

Ser Val Leu Pro Asp Asp Ala Pro Glu Met Asp Glu Ser Phe Leu Ile
                20                  25                  30

Ser Leu Leu
        35
```

<210> SEQ ID NO 20
<211> LENGTH: 35
<212> TYPE: PRT
<213> ORGANISM: Mus musculus

<400> SEQUENCE: 20

```
Asp Ile Leu Thr Phe Ala Glu Gly Glu Thr Lys Lys Met Ala Ile Leu
1               5                   10                  15

Thr Ile Leu Asp Asp Ser Glu Pro Asp Asn Glu Ser Ile Leu Val
                20                  25                  30

Arg Leu Val
        35
```

<210> SEQ ID NO 21
<211> LENGTH: 35
<212> TYPE: PRT
<213> ORGANISM: Mus musculus

<400> SEQUENCE: 21

```
Gly Gln Leu Phe Phe Ser Glu Phe Thr Leu Asn Lys Thr Ile Phe Val
1               5                   10                  15

His Leu Leu Asp Asp Asn Ile Pro Glu Glu Lys Glu Val Tyr Gln Val
                20                  25                  30

Val Leu Tyr
        35
```

<210> SEQ ID NO 22
<211> LENGTH: 35
<212> TYPE: PRT
<213> ORGANISM: Mus musculus

<400> SEQUENCE: 22

```
Gly Ser Leu Val Leu Glu Glu Gly Glu Thr Thr Ala Ala Ile Ser Ile
1               5                   10                  15

Thr Val Leu Glu Asp Asp Ile Pro Glu Leu Lys Glu Tyr Phe Leu Val
                20                  25                  30

Asn Leu Thr
        35
```

```
<210> SEQ ID NO 23
<211> LENGTH: 35
<212> TYPE: PRT
<213> ORGANISM: Mus musculus

<400> SEQUENCE: 23

Gly Thr Leu Val Phe Leu Glu Gly Glu Thr Glu Ala Asn Ile Thr Val
1               5                   10                  15

Thr Val Leu Asp Asp Asp Ile Pro Glu Leu Asp Glu Ser Phe Leu Val
            20                  25                  30

Val Leu Leu
        35

<210> SEQ ID NO 24
<211> LENGTH: 35
<212> TYPE: PRT
<213> ORGANISM: Mus musculus

<400> SEQUENCE: 24

Gly Thr Val Ile Phe Lys Pro Gly Glu Thr Gln Lys Glu Ile Arg Val
1               5                   10                  15

Gly Ile Ile Asp Asp Asp Ile Phe Glu Glu Asp Glu Asn Phe Leu Val
            20                  25                  30

His Leu Ser
        35

<210> SEQ ID NO 25
<211> LENGTH: 35
<212> TYPE: PRT
<213> ORGANISM: Mus musculus

<400> SEQUENCE: 25

Leu Thr Leu Ile Phe Leu Asp Gly Glu Arg Glu Arg Lys Val Ser Val
1               5                   10                  15

Gln Ile Leu Asp Asp Asp Glu Pro Glu Gly Gln Glu Phe Phe Tyr Val
            20                  25                  30

Phe Leu Thr
        35

<210> SEQ ID NO 26
<211> LENGTH: 35
<212> TYPE: PRT
<213> ORGANISM: Mus musculus

<400> SEQUENCE: 26

Gly Glu Pro Glu Phe Glx Asn Asp Glu Ile Val Lys Thr Ile Ser Val
1               5                   10                  15

Lys Val Ile Asp Asp Glu Glu Tyr Glu Lys Asn Lys Thr Phe Phe Ile
            20                  25                  30

Glu Ile Gly
        35

<210> SEQ ID NO 27
<211> LENGTH: 5
<212> TYPE: PRT
<213> ORGANISM: Artificial
<220> FEATURE:
<223> OTHER INFORMATION: consensus sequence
<220> FEATURE:
<221> NAME/KEY: X
<222> LOCATION: (3)..(4)
<223> OTHER INFORMATION: wherein X is any amino acid
```

```
<400> SEQUENCE: 27

Pro Glu Xaa Xaa Glu
1               5

<210> SEQ ID NO 28
<211> LENGTH: 19
<212> TYPE: DNA
<213> ORGANISM: Artificial
<220> FEATURE:
<223> OTHER INFORMATION: synthetic oligonucleotide

<400> SEQUENCE: 28
cagaggatgg atacagtac                                              19

<210> SEQ ID NO 29
<211> LENGTH: 20
<212> TYPE: DNA
<213> ORGANISM: Artificial
<220> FEATURE:
<223> OTHER INFORMATION: synthetic oligonucleotide

<400> SEQUENCE: 29
gtaatctcct ccttgagttg                                             20

<210> SEQ ID NO 30
<211> LENGTH: 19
<212> TYPE: DNA
<213> ORGANISM: Artificial
<220> FEATURE:
<223> OTHER INFORMATION: synthetic oligonucleotide

<400> SEQUENCE: 30
gcagtgtgtt ggcatagag                                              19

<210> SEQ ID NO 31
<211> LENGTH: 18
<212> TYPE: DNA
<213> ORGANISM: Artificial
<220> FEATURE:
<223> OTHER INFORMATION: synthetic oligonucleotide

<400> SEQUENCE: 31
agatcctgac cgagcgtg                                               18

<210> SEQ ID NO 32
<211> LENGTH: 21
<212> TYPE: DNA
<213> ORGANISM: Artificial
<220> FEATURE:
<223> OTHER INFORMATION: synthetic oligonucleotide

<400> SEQUENCE: 32
tttattgtag aggaacctga g                                           21

<210> SEQ ID NO 33
<211> LENGTH: 18
<212> TYPE: DNA
<213> ORGANISM: Artificial
<220> FEATURE:
<223> OTHER INFORMATION: synthetic oligonucleotide

<400> SEQUENCE: 33
gccagtagca aactgtcc                                               18
```

MASS1 GENE, A TARGET FOR ANTICONVULSANT DRUG DEVELOPMENT

RELATED APPLICATIONS

This application is related to and claims the benefit of U.S. Provisional Application Ser. No. 60/187,209 of Louis J. Ptacek, H. Steve White and Ying-Hui Fu, filed Mar. 3, 2000 and entitled "Novel Epilepsy Gene is a Target for Anticonvulsant Drug Development," and U.S. Provisional Application Ser. No. 60/222,898 of Louis J. Ptacek, H. Steve White, Ying-Hui Fu, and Shana Skradski filed Aug. 3, 2000 and entitled "Human mass1 Gene" which are incorporated herein by this reference.

FIELD OF THE INVENTION

The present invention relates to the isolation and characterization of a novel gene relating to epilepsy. More specifically, the invention relates to the isolation and characterization of the Monogenic Audiogenic Seizure-susceptible gene, hereinafter mass1 gene.

TECHNICAL BACKGROUND

Epilepsy is a common neurological disorder that affects nearly 2.5 million people in the United States. Epilepsy is characterized by recurrent seizures resulting from a sudden burst of electrical energy in the brain. The electrical discharge of brain cells causes a change in a person's consciousness, movement, and/or sensations. The intensity and frequency of the epileptic seizures varies from person to person.

Epilepsies in humans can be separated into two forms, symptomatic and non-symptomatic. Symptomatic epilepsy is a seizure disorder related to a known cause such as metabolic disease, brain malformations, or brain tumors. In these cases, seizures presumably occur because of a very abnormal focus (or foci) in the brain. Genetic models of symptomatic epilepsy include the weaver mouse (wv), in which a mutation of the G protein-gated inwardly rectifying potassium channel GIRK2 results in neuro-developmental abnormalities and seizures. Signorini, S. et al. (1997), *Proc Natl Acad Sci USA* 94: 923–7. Fragile X-associated protein knock-out mice have a neurodevelopmental syndrome with lowered thresholds to audiogenic seizures. Musumeci, S. A. et al.(2000), *Epilepsia* 41: 19–23. Audiogenic seizures can also be induced in seizure-resistant mice such as C57BL/6 by repetitive sound stimulation, suggesting that seizure-susceptibility can be influenced by multiple genetic and environmental factors. Henry, K. R. (1967), *Science* 158: 938–40.

Non-symptomatic epilepsies are defined when no structural or metabolic lesions are recognized and the patients have no other neurological findings between seizures. This latter group of patients is more likely to have primary neuronal hyperexcitability that is not caused by metabolic, developmental or structural lesions. Molecular characterization of electrical hyperexcitability in human muscle diseases led to the hypothesis that such disorders might be the result of mutations in neuronal ion channels, the primary determinants of neuronal membrane excitability. Ptacek, L. J. et al. (1991), *Cell* 67: 1021–7.

All non-symptomatic human epilepsy syndromes and genetic mouse seizure models that have been characterized at a molecular level are caused by mutations in ion channels. Ptacek, L. J. (1999), *Semin Neurol* 19: 363–9; Jen, J. & L. J. Ptacek (2000), Channelopathies: Episodic Disorders of the Nervous System. Metabolic and Molecular Bases of Inherited Disease. C. R. Schriver, A. L. Beaudet, W. S. Sly and D. Valle. New York, McGraw-Hill. pp. 5223–5238; Noebels, J. L. (2000), The Inherited Epilepsies. Metabolic and Molecular Bases of Inherited Disease. C. R. Schriver, A. L. Beaudet, W. S. Sly and D. Valle. New York, McGraw-Hill. pp 5807–5832. Some patients with febrile seizures have been recognized to have mutations in sodium channel $\alpha$ and $\beta 1$ subunits while some patients with epilepsy and episodic ataxia were shown to have calcium channel $\beta$-subunit mutations. Wallace, R. H. et al. (1998), *Nat Genet* 19: 366–70; Escayg, A. et al. (2000), *Am J Hum Genet* 66: 1531–9; Escayg, A. et al. (2000), *Nat Genet* 24: 343–5. The voltage-gated potassium channel genes KCNQ2 and KCNQ3, when mutated, result in benign familial neonatal convulsions. Biervert, C. et al. (1998), *Science* 279: 403–6; Charlier, C. et al. (1998), *Nat Genet* 18: 53–5; Singh, N. A. et al. (1998), *Nat Genet* 18: 25–9. Ligand-gated channels can also result in epilepsy as demonstrated by mutations in the $\alpha 4$ subunit of the neuronal nicotinic acetylcholine receptor that result in autosomal dominant nocturnal frontal lobe epilepsy. Steinlein, O. K. et al. (1995), *Nat Genet* 11: 201–3. In mice, the $\alpha$, $\beta$ and $\gamma$ subunits of the voltage-sensitive calcium channel have been associated with the tottering (tg), lethargic (lh) and stargazer (stg) models of absence seizures. Fletcher, C. F. et al (1996), *Cell* 87: 607–17; Burgess, D. L. et al. (1997), *Cell* 88: 385–92; Letts, V. A. et al. (1998), *Nat Genet* 19: 340–7. Finally, audiogenic seizure-susceptibility has been characterized in a mouse knockout model of the 5-HT$_{2C}$ receptor; homozygous mice have audiogenic seizures and altered feeding behavior. Tecott, L. H. et al. (1995), *Nature* 374: 542–6; Brennan, T. J. et al. (1997), *Nat Genet* 16: 387–90.

The Frings mouse represents one of many strains of mice and rats that are sensitive to audiogenic seizures (AGS). These AGS-susceptible rodents represent models of generalized reflex epilepsy and include the well-studied DBA/2 mouse and GEPR-9 rat. The Frings mouse seizure phenotype is similar to other described audiogenic seizes and is characterized by wild running, loss of righting reflex, tonic flexion and tonic extension in response to high intensity sound stimulation Schreiber, R. A. et al. (1980), Genet 10: 537–43. This strain was characterized 50 years ago when it arose as a spontaneous mutation on the Swiss Albino background. Frings, H. et al. (1951), *J Mammal* 32: 60–76. Selective inbreeding for seizure-susceptibility produced the current homozygous Frings strain with >99% penetrance of audiogenic seizures. The Frings mouse seizure phenotype was due to the autosomal recessive transmission of a single gene.

Audiogenic seizures have been observed in polygenic rodent models, such as the DBA/2 mouse and GEPR-9 rat. Collins, R. L. (1970), *Behav Genet* 1: 99–109; Seyfried, T. N. et al. (1980), *Genetics* 94: 701–718; Seyfried, T. N. & G. H. Glaser (1981), *Genetics* 99: 117–126; Neumann, P. E. & T. N. Seyfried (1990), *Behav Genet* 20: 307–23; Neumann, P. E. & R. L. Collins (1991), *Proc Natl Acad Sci USA* 88: 5408–12; Ribak, C. E. et al. (1988), *Epilepsy Res* 2: 345–55. While no genes associated with audiogenic seizures in spontaneous mutant models have been cloned, three putative loci associated with seizure-susceptibility in the DBA/2 mouse (asp1, asp2, and asp3) have been mapped to chromosomes 12, 4, and 7, respectively. Neumann & Seyfried, supra; Neumann, P. E. & R. L. Collins, supra. As a monogenic audiogenic seizures model, the Frings mice provided a unique opportunity for cloning and characterization of an audiogenic seizures gene. The Frings mice are an important naturally occurring monogenic model of a discrete non-symptomatic epilepsy and provide significant information on a novel mechanism of seizure-susceptibility as well as central nervous system excitability in general.

In light of the foregoing, it will be appreciated that it would be an advancement in the art to identify and characterize nucleic acid sequences that are associated with the monogenic AGS susceptibility in Frings mice. It would be a further advancement to identify and characterize the human orthologue of this gene. It would be a further advancement if the nucleic acid sequences could provide additional understanding of how epileptic seizures are triggered in disease. It would be a further advancement to provide a transgenic animal model wherein the endogenous gene associated with the Frings phenotype is mutated.

Such nucleic acid sequences and animals are disclosed and claimed herein.

BRIEF SUMMARY OF THE INVENTION

The present invention relates to an isolated novel gene which has been imputed in audiogenic seizure-susceptibility in mice known as the mass1 gene. Provided herein are nucleic acid molecules that encode the MASS1 protein. The nucleic acid molecules of the present invention may also comprise the nucleotide sequence for human mass1 (SEQ ID NO: 3) and murine mass1 (SEQ ID NO: 1). In certain other embodiments, the present invention provides nucleic acid molecules that code for the amino acid sequence of human MASS1 (SEQ ID NO: 4) and murine MASS1 (SEQ ID NO: 2). The invention also provides nucleic acid molecules complementary to the nucleic acid molecules of SEQ ID NO: 3 and SEQ ID NO: 1. The invention also relates to other mammalian mass1 genes and MASS1 proteins.

The present invention also relates to an isolated nucleic acid having at least 15 consecutive nucleotides as represented by a nucleotide sequence selected from the nucleotides of the murine mass1 gene (SEQ ID NO: 1) and the nucleotides of the human mass1 gene (SEQ ID NO: 3). A nucleotide having in the range from about 15 to about 30 consecutive nucleotides as represented by a nucleotide sequence selected from the nucleotides of the murine mass1 gene (SEQ ID NO: 1) and the nucleotides of the human mass1 gene (SEQ ID NO: 3) is also within the scope of the present invention.

The present invention also provides recombinant vectors comprising nucleic acid molecules that code for MASS1. These recombinant vectors may be plasmids. In other embodiments, these recombinant vectors are prokaryotic or eukaryotic expression vectors. The nucleic acid coding for MASS1 may also be operably linked to a heterologous promoter. The present invention further provides host cells comprising a nucleic acid that codes for MASS1.

The present invention also relates to a transgenic mammal with a mutation in one or both alleles of the endogenous mass1 gene. The mutation in one or both of the endogenous mass1 genes may result in a mammal with a seizure-susceptible phenotype. The transgenic mammal of the present invention may be a mouse. The mutation may result from the insertion of a selectable marker gene sequence or other heterologous sequence into the mammal's genome by homologous recombination. The invention also provides cells derived from the transgenic mammal.

These and other advantages of the present invention will become apparent upon reading the following detailed description and appended claims.

SUMMARY OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

FIG. 6 illustrates the conceptual amino acid translation of the mass1.1 transcript (SEQ ID NO: 5). The 18 MASS1 repetitive motifs are boxed with a solid line and the 2 less conserved possible repeats are boxed with a dashed line. The putative multicopper oxidase I domain is underlined. The valine→stop mutation in the Frings MASS1 protein is located at amino acid number 1072 marked with the "*".

Figure 1:
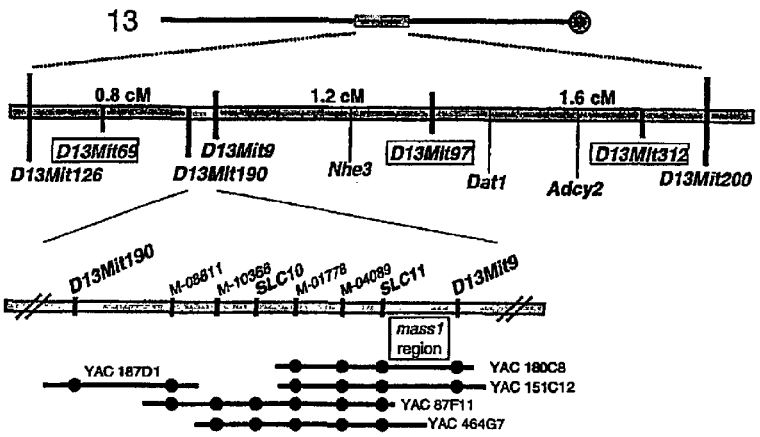
FIG. 1 shows a linkage map of the mass1 locus initially defined by markers D13Mit126 and D13Mit200. Markers D13Mit69, 97, and 312 (enclosed in rectangles) were used to genotype the F2 progeny. The estimated genetic distances are shown. The location of candidate genes Nhe3, Dat1, and Adcy2 are indicated. The map inset represents the large-scale physical map of the mass1 interval spanned by yeast artificial chromsomes (YACs). SLC10 and SLC11 are novel SSLP markers, and the others are STS markers.

FIG. 7 illustrates the amino acid sequence alignment of the MASS1 repeats. (SEQ ID NOS: 6–23). The first 18 lines represent the well conserved amino acid repeat motif found in MASS1. Positions of highly conserved amino acids are shaded gray. The next line shows the consensus sequence for the MASS1 repeat (SEQ ID NO: 24), and below it are the sequences of the $Na^+/Ca^{2+}$ exchanger (β1 and β2) segments that share homology with the MASS1 repeat (SEQ ID NOS: 25 & 26). Also shown is a homologous region of the very large G-protein coupled receptor-1 (Accession 55586) (SEQ ID NO: 27). The boxed segment outline the DDD motif that has been shown to be a $Ca^{2+}$ binding site in the $Na^+/Ca^{2+}$ exchanger β1 segment.

DETAILED DESCRIPTION OF THE INVENTION

The present invention relates to DNA for a novel Monogenic Audiogenic Seizure-susceptible gene (mass1). More particularly, the present invention relates to the isolation and characterization of the mouse mass1 gene (SEQ ID NO: 1) and the human mass1 gene (SEQ ID NO: 3). The discovery that the murine mass1 gene is mutated in Frings mice suggests that mass1 has a role in seizure susceptibility.

Nucleotide sequences complementary to the nucleotide sequences of SEQ ID NO: 1 and SEQ ID NO: 3 are also provided. Isolated and purified nucleotide sequences that code for the amino acid sequence of the mouse MASS1 (SEQ ID NO: 2) protein are also within the scope of the invention. Nucleotide sequences that code for the amino acid sequence of the human MASS1 (SEQ ID NO: 4) protein are within the scope of the invention. A nucleic acid sequence that codes for MASS1 of any mammal is also within the scope of the invention.

The nucleic acid molecules that code for mammalian MASS1 proteins, such as a human or murine MASS1, can be contained within recombinant vectors such as plasmids, recombinant phages or viruses, transposons, cosmids, or artificial chromosomes. Such vectors can also include elements that control the replication and expression of the mass1 nucleic acid sequences. The vectors can also have sequences that allow for the screening or selection of cells containing the vector. Such screening or selection sequences can include antibiotic resistance genes. The recombinant vectors can be prokaryotic expression vectors or eukaryotic expression vectors. The nucleic acid coding for MASS1 can be linked to a heterologous promoter.

Host cells comprising a nucleic acid that codes for mammalian MASS1 are also provided. The host cells can be prepared by transfecting an appropriate nucleic acid into a cell using transfection techniques that are known in the art. These techniques include calcium phosphate co-precipitation, microinjection, electroporation, liposome-mediated gene transfer, and high velocity microprojectiles.

The Frings mouse is unique among rodent epilepsy models. It is a naturally-occurring single gene model of audiogenic generalized seizures without any other associated neurological or behavioral phenotypes. Sequencing of cosmids from the nonrecombinant mass1 interval identified a single gene. Until recently, computer-based BLAST nucleotide sequence similarity searches did not identify significant similarity between the mass1 sequence and any other sequences in the databases. The deficiency of mass1 cDNA sequence in the databases further supports the hypothesis that mass1 is expressed in low abundance in the brain or that it is degraded very rapidly. This hypothesis is based on the fact that screening two independent brain cDNA libraries for the mass1 cDNA did not produce any positive clones, and low message levels were further supported by Northern blots, RT-PCR, and in situ hybridization. The low abundance could be due to low expression of the mass1 mRNA, or to the message being unstable and quickly degraded.

The mass1 gene was identified by positional cloning and sequencing, exon prediction, RT-PCR and PCR-based 5' and 3' RACE. Screening several cDNA libraries by hybridization had not identified a mass1 CDNA clone. Despite not finding a cDNA clone in the cDNA libraries, convincing data implicates mass1 as the gene causing AGS in the Frings mice. Mass1 is the only gene found in the small non-recombinant mass1 interval. The cDNA from both mouse and human Marathon cDNA libraries (Clontech, Palo Alto, Calif.) can be amplified. The intron-exon boundaries are conserved for the genomic structure of hMass1. The alternate transcript of mouse mass1 exon 27 is also found in hMass1. The mass1 transcripts contain long open reading frames which are disrupted by a single base-pair deletion in the Frings mouse.

Figure 2:
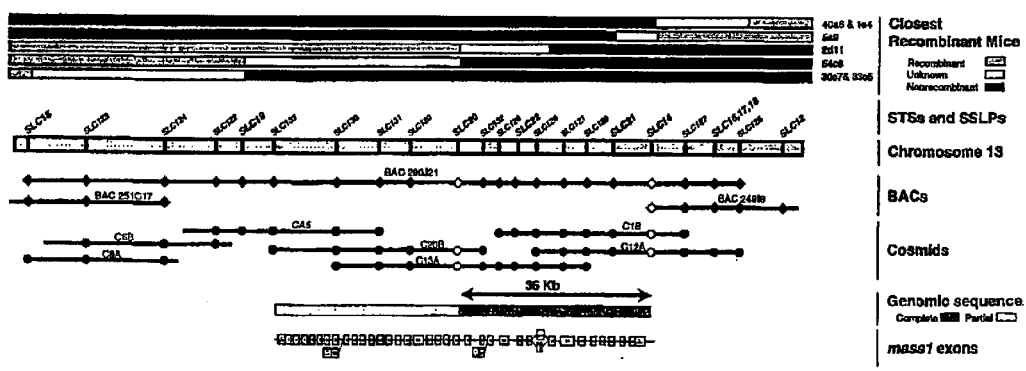
FIG. 2 is a fine-scale physical map of the mass1 interval defined by bacterial artificial chromosomes (BACs) and cosmids. SLC-numbers between 10 and 100 are novel SSLP markers, and SLC-numbers 100 to 200 are novel STS markers. The bars above the map represent the genotypes of the nearest recombinant mice. The gray bars represent regions where the mice are recombinant, black filled bars are regions where the mice are nonrecombinant, and white filled bars are regions where the markers were not informative. The final mass1 interval was spanned by cosmids C13A and C1B, and the complete genonic sequence was generated between the markers SLC20 and SLC14. The alignment of the mass1 exons that were identified from the sequence are shown at the bottom.

PCR approaches have been required to clone all or parts of other genes such as the melatonin receptor. Reppert, S. M. et al. (1994), *Neuron* 13: 1177–85. In such cases, results must be viewed with caution because of artifacts inherent with PCR-based assays. Problems include producing inaccurate sequence due to Taq DNA polymerase errors and errors due to amplifying parts of homologous genes. To avoid these problems, the mass1 final sequence was compiled from segments amplified with a high fidelity Pfx DNA polymerase (Gibco) to produce accurate sequence from multiple templates. The mass1 cDNA sequence matched exactly with predicted exons from genomic sequencing of cosmids C1B, C13A, and C20B (FIG. 2).

The homology of the MASS1 protein sequence repetitive motifs to the sodium$^+$-calcium$^{2+}$ exchanger ($Na^+/Ca^{2+}$ exchanger) β1 and β2 repeat domains may provide an important clue toward identifying the function of this novel protein. Although the identity between these proteins is limited to a short segment of the cytosolic loop of the exchanger, it is likely to be functionally significant in MASS1 because this motif is repeated 18 times within the protein sequence (FIGS. 6 and 7). The $Na^+/Ca^{2+}$ exchanger is a plasma membrane associated protein that co-transports three sodium ions into a cell and one calcium ion out of the cell using the sodium electrochemical gradient. Nicoll et al., supra. The $Na^+/Ca^{2+}$ exchanger can be regulated by intracellular calcium at a $Ca^{2+}$ binding site on the third cytosolic loop that is distinct from the $Ca^{2+}$ transport site. This binding site is composed of three aspartate residues (DDD) (FIG. 7). When $Ca^{2+}$ is bound at this site, the transporter is activated. Matsuoka, S. et al. (1993), *Proc Natl Acad Sci USA* 90: 3870–4; Levitsky, D. O. et al. (1994), *J Biol Chem* 269: 22847–52; Matsuoka, S. et al. (1995), *J Gen Physiol 105:* 403–20. One of the MASS1 repeats contains the DDD motif, and three others have conservative D to E substitutions suggesting that these domains may be involved in $Ca^{2+}$ binding.

The multicopper oxidase I consensus sequence identified within the MASS1 amino acid sequence is also an interesting putative functional domain. The multicopper oxidases represent a family of proteins that oxidize substrates while reducing molecular $O_2$ to $H_2O$. The oxidation of multiple substrate molecules occurs serially while storing electrons in the copper atom (presumably to prevent the formation of reactive species) until a molecule of $O_2$ is reduced. Two known multicopper oxidases, Fet3p in yeast and ceruloplasmin in humans, have been shown to oxidize and transport iron. Askwith, C. et al. (1994), *Cell* 76: 403–10; Harris, Z. L. et al. (1995), Proc Natl Acad Sci USA 92: 2539–43. A third multicopper oxidase, hephaestin has been suggested to be a feroxidase. Vulpe, C. D. et al. (1999), *Nat Genet* 21: 195–9. Other known multicopper oxidase substrates include $Mn^{2+}$, serotonin, epinephrine, dopamine, and (+)-lysergic acid diethylamide (LSD). Zaitsev, V. N. et al. (1999), *J Biol Inorg Chem* 4: 579–87; Brouwers, G. J. et al. (1999), *Appl Environ Microbiol* 65: 1762–8. Therefore, loss of this putative functional domain could possibly result in problems with the metabolism of iron or other metals, copper sequestration, neurotransmitter processing, and/or oxidative stress. Furthermore, the tyrosine kinase and cAMP/cGWP dependent phosphorylation sites may be functionally significant. However, with a large protein such as MASS1, similarities and identities to functional domains commonly occur by chance, and detailed biochemical analysis of the protein will be required to determine which of these motifs are functional domains.

The human orthologue of the mass1 gene resides on chromosome 5q. Interestingly, a gene causing a human epilepsy has also been mapped to this region of chromosome 5. This locus, FEB4, was mapped in families with a phenotype of febrile convulsions. Nakayama, J. et al. (2000), *Hum Mol Genet* 9: 87–91. While this temperature-sensitive phenotype is different than audiogenic seizures, hmass1 will be an important candidate to test in the FEB4-linked families.

To date, all genes that have been shown to cause non-symptomatic epilepsies have encoded ion channels (voltage- or ligand-gated and exchangers). Jen & Ptacek, supra; Noebels, supra. The mass1 gene therefore represents the first novel gene shown to cause a non-symptomatic epilepsy. The seizures in the Frings mice are different from those recognized to be caused by ion channels. The phenotype is a reflex epilepsy with seizures in response to loud auditory stimuli. This suggests that the genesis of episodes may be in brainstem rather than being due to hyperexcitability of cortical neurons. There is a growing appreciation of the role that deep brain structures and brainstem play in the integration and modulation of cortical discharges. For example, normal synchronized discharges are seen in EEGs of sleeping individuals. Perhaps some of the reflex epilepsies in humans are not the result of primary cortical hyperexcitability, but rather, of abnormal function of circuits critical for integration and modulation of cortical activity. Much work will be required to test this hypothesis, but some fascinating episodic CNS disorders have clinical and electrical manifestation that may be consistent with this idea. Fouad, G. T. et al. (1996), *Am. J. Hum. Genet.* 59: 135–139; Ptacek, L. J. (1998), Genetics of Focal Epilepsies. P. Genton. London, John Libbey. pp 203–13; Plaster, N. M. et al. (1999), *Neurology* 53: 1180–3; Swoboda, K. J. et al. (2000), *Neurology* 55: 224–30.

Identification and characterization of the mass1 gene reveals it to be novel and rare transcript. Further research to determine the function of MASS1 will lead to understanding of how a defect in this protein results in seizures in these audiogenic seizure-susceptible mice. From the mouse mass1 cDNA, a partial human mass1 homolog has been identified. Through mapping and characterization of the human homolog, it may be possible to find an association of mass1 with a human epilepsy disorder. Together, the studies of the mouse and human MASS1 will provide insight into the function of this novel protein and is likely to lead to new insights into normal neuronal excitability and dysfunction of membrane excitability that can lead to seizures and epilepsy.

The present invention also provides transgenic mice in which one or both alleles of the endogenous mass1 gene are mutated. Such animals are useful for example to further study the physiological effects of this gene or to test potential drug candidates.

Methods for making such transgenic animals are known in the art. See, e.g., Hogan et al., *Manipulating the Mouse Embryo: A Laboratory Manual* (2d ed. 1994); Hasty et al. (1991), *Nature* 350:243–246; Mansour et al. (1988), *Nature* 336:348–352. Briefly, a vector containing the desired mutation is introduced into mouse embryonic stem (ES) cells. In some of these stem cells, the desired mutation may be introduced into the cell's genome by homologous recombination. Stem cells carrying the desired mutation may be identified using selection and/or screening procedures. Such cells are then injected into a blastocyst, which may develop into a chimeric mouse with some of the mouse's cells carrying the desired mutation. A chimeric animal carrying germ cells with the desired mutation may be bred to produce mutant offspring.

Vectors containing a desired mutation may be produced using methods known in the art. See, e.g., 1–3 Sambrook et al., *Molecular Cloning: A Laboratory Manual* (2d ed. 1989). Such vectors would typically include a portion of the mouse mass1 gene to facilitate homologous recombination between the vector and endogenous gene sequences. A selectable marker may be used to disrupt the coding sequence or an expression control element of the mass1 gene. Suitable selectable markers are known in the art. For example, the Neomycin resistance gene (neo), which encodes Aminoglycoside phosphotranferase (APH), allows selection in mammalian cells by conferring resistance to G418 (available from Sigma, St. Louis, Mo.). Other suitable markers may also be used to disrupt the mass1 gene. Techniques have also been developed to introduce more subtle mutations into genes. See, e.g., Hasty et al., supra.

Vectors may also include sequences to facilitate selection or screening of ES cells in which the desired mutation has been introduced by homologous recombination. For example, a vector may include one or more copies of a gene such as the herpes simplex virus thymidine kinase gene (HSV-tk) upstream and/or downstream of the mass1 gene sequences. As illustrated in Mansour et al., supra, random integration events would lead to incorporation of the HSV-tk gene into the ES cell genome, while homologous recombination events do not. ES cells carrying randomly integrated vectors (and, therefore, HSV-tk), may be selected against by growing the cells in a medium supplemented with gancyclovir.

A vector containing the desired mutation may be introduced into ES cells in any of a number of ways. For example, electroporation maybe used. See Mansour et al., supra. Other techniques for introducing vectors into cells are known in the art, including viral infection, calcium phosphate co-precipitation, direct micro-injection into cultured cells, liposome mediated gene transfer, lipid-mediated transfection, and nucleic acid delivery using high-velocity microprojectiles. Graham et al. (1973), Virol. 52:456–467; M. R. Capecchi (1980), *Cell* 22:479–488; Mannino et al. (1988), *BioTechniques* 6:682–690; Felgner et al. (1987), *Proc. Natl. Acad Sci. USA* 84:7413–7417; Klein et al. (1987), *Nature* 327:70–73.

Techniques for preparing, manipulating, and culturing ES cells have been described. See, e.g., Hogan et al., supra; Mansour et al., supra. ES cells carrying the desired mutation may be identified by screening or selection methods that are known in the art, including growth in selective media and screening using PCR-based or DNA hybridization (Southern blotting) techniques.

In order to better describe the details of the present invention, the following discussion is divided into six sections: (1) fine mapping and physical mapping of mass1; (2) candidate gene indentification; (3) cloning and analysis of mass1 CDNA; (4) mapping of the hMass1 gene; (5) identification of a mass1 mutation in DNA from Frings mice; and (6) analysis of the mass1 translated protein sequence.

6.1 Fine Mapping & Physical Mapping

Referring to FIG. 1, the mass1 interval between D13Mit200 to D13Mit126 was estimated to be 3.6 cM with the initial set of 257 N2 mice tested. Skradski, S. L. et al. (*1998*), *Genomics* 49: 188–92. Approximately 1200 additional (Frings X C57BL/6J)F1 intercross mice were genotyped with microsatellite markers D13Mit312, D13Mit97, and D13Mit69 that span the interval. Analysis of the recombinations determined that the mass1 region was distal to the D13Mit97 marker and proximal of D13Mit69. Two additional microsatellite markers, D13Mit9 and D13Mit190, were identified within this interval from the Chromosome 13 Committee map. Genotyping of the border-defining recombinant mice with these markers narrowed the interval to between D13Mit9 and D13Mit190. Of the 1200 F2 mice, three were recombinant at D13Mit9 and ten mice were recombinant at D13Mit190. No other known simple sequence length polymorphisms (SSLPs) markers were mapped within this interval.

This distance between the markers D13Mit9 and D13Mit190 was covered by three overlapping YACs 151C12, 87F11, and 187D1 found on the contig WC13.27. These YACs contained four known sequence-tagged sites (STSs), SLC106, SLC117, SLC111 and SLC105 shown in FIG. 2. The four STSs were used to identify BACs from the BAC library. A new single nucleotide polymorphisms was screened by sequencing small-insert pUC19 subclone libraries of the BACs. Two newly identified polymorphic markers, SLC10 and SLC11, were identified and further narrowed the distal border and defined the mass1 interval to the distance spanned by a single YAC, 151C12, between markers SLC11 and D13Mit9 as shown in FIG. 1.

Since no known SSLPs or STSs were contained within the mass1 interval, a physical map of the region was constructed by using end sequences of BAC clones to develop new STSs to re-screen the library for overlapping BACs. Simultaneous with the physical mapping, identification of SSLPs from the new BACs continued to narrow the interval. Seven overlapping BACs were required to cover the distance between SLC11 and D13Mit9. SSLPs from each end of the insert of BAC 290J21, SLC14 and SLC15, were recombinant and localized the mass1 gene to this small region as shown in FIG. 2. Based on the insert size of the BAC, this narrowed the mass1 region to less than 150 Kb.

This BAC insert was subcloned into both a cosmid vector and pUC19. Sequences from randomly selected pUC19 clones were used to develop new STSs across the BAC, and these new markers were then used to align cosmids into a complete contiguous map of BAC 290J21 as shown in FIG. 2. SSLP screening of the pUC19 library detected five new repeat markers within BAC 290J21 (SLC16–20). Two of these, SLC19 and SLC20, were mapped within the mass1 interval. Analysis of recombinants at these markers showed a recombination with SLC20 that refined the interval to two overlapping cosmids, C1B and C13A, between the markers SLC14 and SLC20 each with a single recombinant mouse (5a9 and 2d11).

6.2 Candidate Gene Identification

Intragenic STS markers were developed for known candidate genes (Dat1, Adcy2, and Nhe3) that mapped to the general region containing mass1. PCR analysis of the STSs showed that none of the YACS, BACs or cosmids comprising the physical map contained these genes. To directly identify candidate genes from the two cosmids, C1B and C13A, mouse brain cDNA libraries were screened by hybridization using cosmid DNA as probe. The library screening experiments were unsuccessful at identifying any candidate cDNAs from the region, therefore, an alternate strategy of shot-gun subcloning and sequencing of cosmids C1B and C20B was employed.

The cosmid sequences were edited and compiled to produce the complete genomic sequence from marker SLC14 to SLC20. The complete nonrecombinant mass1 interval was approximately 36 Kb. Analysis of the sequence by the exon-finding program, Genefinder, predicted one multiple-exon gene spanning the mass1 interval oriented from the distal to proximal end. Reverse transcription-PCR (RT-PCR) with primers spanning putative introns amplified products of the appropriate sizes from Frings and C57/BL/6J total brain RNA. Sequence analysis of these bands confirmed that they matched the genomic sequence within the exons and identified the first intronexon boundries.

6.3 Cloning and Analysis of mass1 cDNA

RT-PCR experiments produced 1 Kb of open reading frame that could be amplified from mouse brain RNA. Subsequently, rapid amplification of cDNA ends (RACE) defined the 3' end of the gene which contained 330 base pairs of untranslated sequence from the first stop codon to the polyA tail. Multiple 5' RACE reactions produced the complete cDNA sequence of mass1 and identified three putative alternate transcripts each containing a unique 5' untranslated sequence. When the cDNA sequence was aligned with 36 Kb of complete genomic sequence from cosmid C1B, 15 exons were noted to correspond the 3' end of the cDNA sequence; primers were designed from the remaining 5' cDNA sequence and used to sequence cosmid C20B. Analysis of this genomic sequence revealed 20 exons as shown in FIG. 2. Thus the longest transcript is composed of 35 exons.

The mass1 gene encodes three putative alternate transcripts. The longest transcript is approximately 9.4 Kb, the second 7.1 Kb, and the shortest 3.7 Kb. Northern blot analyses of mouse RNA failed to produce conclusive data to confirm these transcript sizes and suggested that the transcript levels were very low. However, several autoradiograms with very long exposure times (3–4 weeks) suggested that the 9.4 and 7.1 Kb transcripts are expressed in mouse brain (data not shown). In situ hybridizations using a 3 Kb product from the 3' end of the cDNA to probe mouse brain did not reveal any signal above background further suggesting the mRNA levels to be very low.

Figure 3:
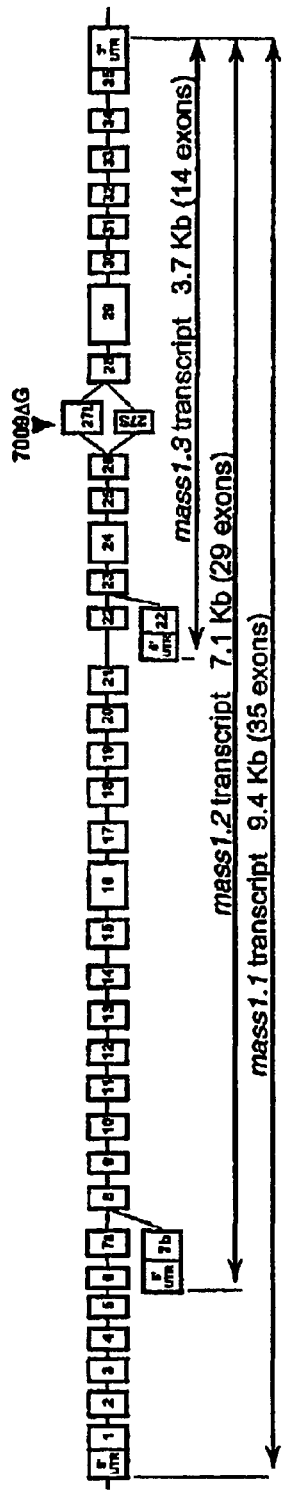
FIG. 3 is a diagram of the mass1 genomic structure showing three putative transcripts and exons that are included in each transcript. The short transcript, mass1.3, has putative 5' untranslated sequence leading into exon 22. Exon 7a and 7b represent two alternate exons that have been identified in mouse brain cDNA. The medium transcript, mass1.2, has putative 5' untranslated sequence leading into exon 7b, and the longest transcript, mass1.1, has only been shown to contain exon 7a. A long and short splice variant was identified in exon 27 (27L and 27S). The 27S variant removes 83 base pairs and changes the reading frame.

Each putative transcript contains a unique 5' untranslated region leading into the rest of the gene sequence. All three transcripts contain a possible splice variant in exon 27 where 83 base pairs of sequence are either included (27L) or removed (27S) from the transcript as illustrated in FIG. 3.

Figure 4:
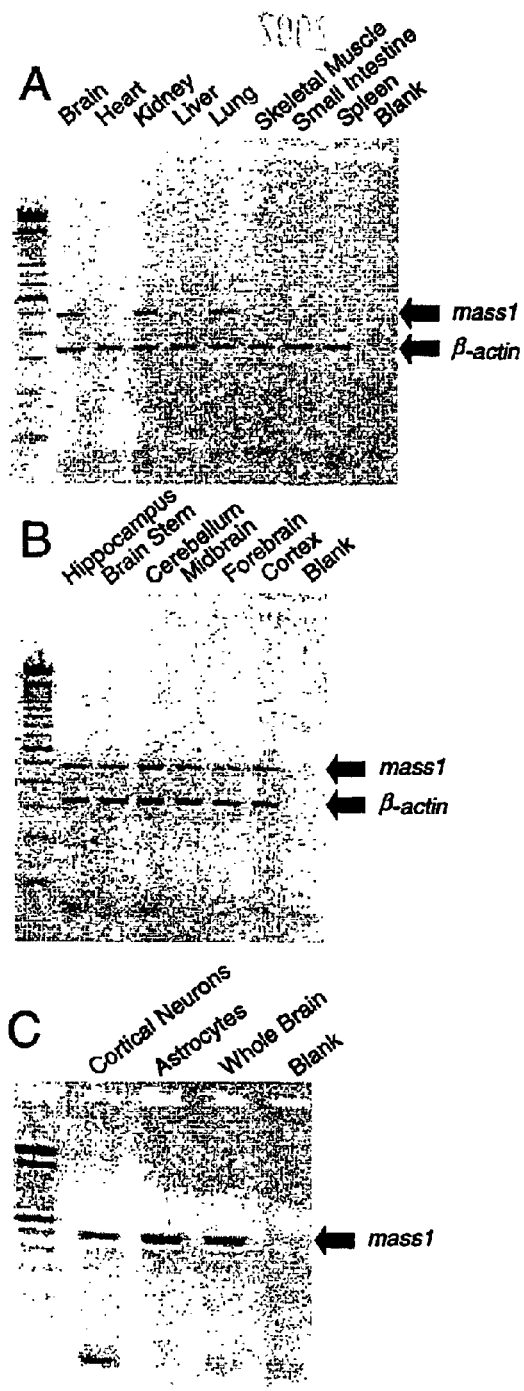
FIG. 4A illustrates expression analysis of the mass1 gene by RT-PCR in different tissue and cell RNA samples using primers from exons 23 and 24. Analysis of mass1 in multiple tissue RNA samples of a CF1 mouse shows expression is primarily in the brain, kidney, and lung, and not in the other tissues listed
FIG. 4B illustrates further expression analysis of the mass1 gene by RT-PCR using brain RNA. Mass1 expression was detected in all regions of the brain tested.
FIG. 4C illustrates expression analysis by RT-PCR of the mass1 gene with pooled cultured cortical neuron RNA and cultured astrocyte RNA compared to whole brain. The mass1 specific primers span intron 23 and the expected product size was 487 base pairs. The β-actin primers also spanned two exons and the expected product size is 327 base pairs. The ladder is in 100 base pair increments.

Referring to FIG. 4A, analysis of the expression of mass1 in mouse tissues by RT-PCR of brain, heart, kidney, liver, lung, muscle, intestine, and spleen RNA shows that the gene is predominantly found in the brain, lung, and kidney. Further analysis of the adult mouse brain showed ubiquitous mass1 expression throughout the mouse brain region including hippocampus, brain stem, cerebellum, midbrain and cortex as shown in FIG. 4B. Reverse transcription and PCR revealed mass1 transcripts to be present in RNA isolated from cultured astrocytes and in RNA aspirated and isolated from single mouse cultured cortical neurons as shown in FIG. 4C.

6.4 Mapping of the hMass1 Gene

A human genomic clone containing the human homolog of the mass1 gene was identified by screening a BAC library by PCR with primers from the mouse mass1 gene under lower stringency. This clone was used in flourescent in situ hybridization experiments and mapped to human chromosome 5q14.

6.5 Identification of a mass1 Mutation in DNA from Frings Mice

Figure 5:
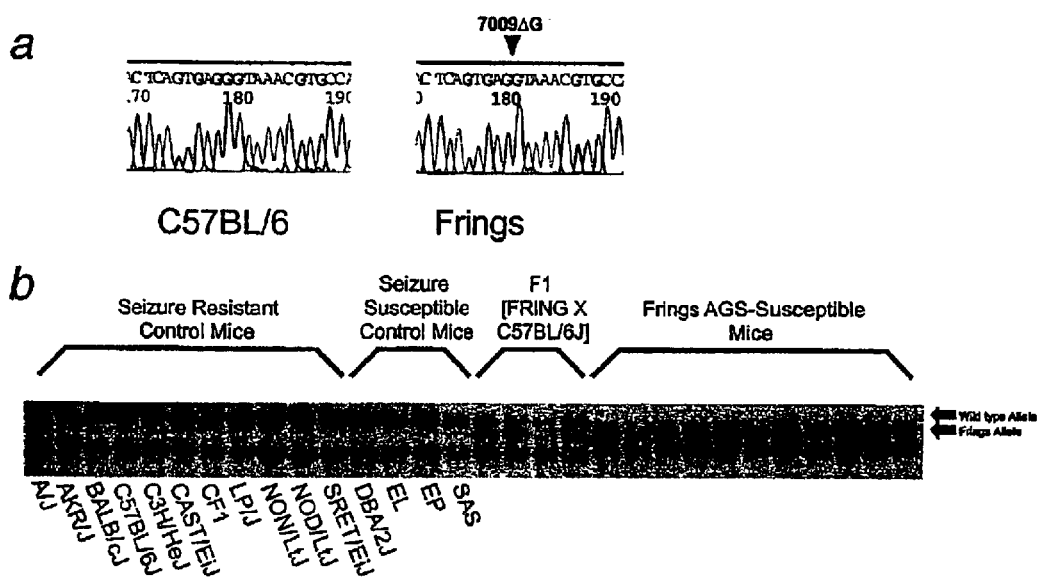
FIG. 5A is a sequence chromatogram of the exon 27 segment from C57BL/6J and Frings DNA. The sequence chromatogram illustrates the identification of a single base pair deletion found in exon 27 of mass1 sequence of Frings mice. The Frings mouse DNA contains a single G deletion at nucleotide 7009.
FIG. 5B illustrates high resolution gel electrophoresis of PCR products from a 150 base pair segment of exon 27 encompassing 7009ΔG, showing that none of the seizure-resistant and seizure-susceptible control mouse DNA samples harbor the deletion present in the Frings mouse.

Seventeen single nucleotide polymorphisms (SNPs) were identified between Frings and C57BL/6J mice within the nonrecombinant coding region, exons 21 to 35. One of these SNPs was a single base pair deletion detected in the Frings mouse mass1 gene by sequence analysis of PCR products. FIG. 5A shows the sequence chromatogram of this single G deletion at position 7009 in the Frings mouse DNA sample compared to the seizure-resistant control C57BL/6J. This deletion results in a frame shift of the open reading frame changing the valine to a stop codon; this change is expected to produce a truncated MASS1 protein in Frings mice. Further analysis of the deletion in other mouse strains by gel electrophoresis showed that the deletion is only detected in Frings mouse DNA and not in any of the other seizure-resistant or seizure-susceptible mouse strains tested as shown in FIG. 5b. The deletion is located in exon 27 before the long and short splice variants. Of the other SNPs identified, six altered the amino acid sequence of the protein and could, theoretically, be the genetic basis of Frings audiogenic seizure-susceptibility. Otherwise, these changes represent polymorphisms that may produce subtle alterations in the function of the protein.

6.6 Analysis of the mass1 Translated Protein Sequence

The mass1 gene produces three putative transcripts: mass1.1 (9.4 Kb), mass1.2 (7.1 Kb), and mass1.3 (3.7 Kb). The long transcript contains 9327 nucleotides and is expected to produce an approximately 337 kilodalton (kD) protein. The medium transcript contains 6714 nucleotides and the predicted protein size is 244 kD. The short transcript open reading frame is 2865 nucleotides and the predicted protein size is approximately 103 kD. These transcripts and isoforms are based on incorporation of the longer splice form of exon 27 (27L). Further putative variants are possible as a result of the 27S alternate splicing event. Using the 27S exon theoretically shortens all the transcripts by 83 nucleotides and each of the isoforms by 645 amino acids (approximately 69.4 kD). The conceptual translation of the amino acid sequence for the mass1.1(27L) transcript is shown in FIG. 6. The MASS1 protein is strongly acidic and has a −192 charge at pH 7.0. The hydropathy plot indicated numerous hydrophobic domains that are candidates for transmembrane segments.

Database searches using the mass1.1 sequence identified no expressed sequence tags (ESTs) that were identical and no homologous genes. However, a small repetitive motif from MASS1 shared homology with numerous $Na^+/Ca^{2+}$ exchangers. This homology was to the β1 and β2 repeats in the third cytosolic loop of the exchanger that contains the $Ca^{2+}$ regulatory binding domain. Nicoll, D. A. et al. (1996), Ann NY Acad Sci 779: 86–92. Further analysis of MASS1 determined that this motif occurs 18 times within the sequence. Alignment of these sequences shows several highly conserved amino acids within this motif (FIG. 7) including a Proline-Glutamate-X-X-Glutamate (PXXE) amino acid sequence (SEQ ID NO: 28) that is preceded by one to three acidic residues (D or E). The proline and first glutamate are completely conserved in all 18 related motifs, and the second glutamate is conserved in 16 of the motifs. In repeats 10 and 11, a lysine is substituted for the second glutamate. The PEXXE motif occurs twice more within the MASS1 sequence, however, these repeats (repeats 19 and 20) have a lower degree of identity and similarity (FIG. 6).

Three aspartic acid residues (DDD) are found in the $Na^+/Ca^{2+}$ exchanger β1 segment and in the segment of the very large G-protein coupled receptor-1 directly preceding the PEXXE motif. In the MASS1 repeat, however, this DDD motif is not well conserved with only repeat number 3 containing the exact DDD motif, and repeats 1, 9, and 18 containing conservative substitutions of glutamate residues. The 18 repeats are distributed across the MASS1 protein and repeats 14 to 18 would be missing from the truncated MASS1 protein (FIG. 6).

Analysis of the MASS1 sequence by Pattern Match identified a multicopper oxidase I consensus sequence site in the carboxyl-terminal region of MASS1. The multicopper oxidase I site is located in exon 29 (FIG. 6), within the region of the MASS1 protein that would be truncated by the Frings 7009ΔG mutation. Frings mice would therefore be lacking this potentially important domain. Biochemical analysis of this putative domain will determine if this is a functional multicopper oxidase I domain. Other less common motifs found within MASS1 include three tyrosine kinase phophorylation motifs, two cAMP/cGMP-dependent phosphorylation motifs, and one glycosaminoglycan attachment motif. Finally, numerous common putative protein modification sites were identified including casein kinase II phosphorylation, protein kinase C phosphorylation, N-myristylation, and N-glycosylation sites. Further analysis of the MASS1 protein will be required to determine if any of these consensus sites are functional.

All patents, publications, and commercial materials cited herein are hereby incorporated by reference.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Mouse Breeding, Seizure Testing and DNA Collection

Frings mice were crossed to the seizure-resistant stain C57BL/6J to produce F1 animals which, in turn, were intercrossed to generate 1200 F2 offspring. The Frings mice used in this study were bred in our colony and the C57BL/6J mice were supplied by the Jackson Laboratory (Bar Harbor, Me.). All mice were phenotyped at postnatal day 21 as seizure-susceptible or seizure-resistant as described previously. Skradski, S. L. et al., supra. Directly following seizure phenotyping, tail sections were cut for DNA preparation. Potential recombinant mice within the region were tested again to confirm the seizure phenotype, a second tail section was cut, and the mice were euthanized by $CO_2$ and bilateral thoracotomy. Spleens were harvested for DNA preparation by phenol/chloroform extraction and ethanol precipitation

Example 2

Fine Mapping

All known MIT microsatellite markers between cD13Mit200 and D13Mit126 were identified from the Chromosome 13 Committee map publicly available at the Mouse Genome Informatics Website. All F2 mice were initially tested with polymorphic markers D13Mit312, D13Mit97, and D13Mit69 to identify recombinant mice in the mass1 region, and the new recombinant mice were genotyped with additional markers, D13Mit9 and D13Mit190. Primer sequences and information for the markers was obtained from the Whitehead Institute Database site Genetic and Physical Maps of the Mouse Genome. Primer synthesis and SSLP analysis was performed as previously described. Skradski, S. L. et al., supra.

Example 3

Yeast Artificial Chromosomes

YAC maps spanning the region were obtained from the Genetic and Physical Maps of the Mouse Genome website. YACs which appeared to contain SSLP markers known to be within the region were obtained from Research Genetics and YAC DNA was prepared by standard techniques. Haldi, M. L. et al. (1996), *Mamm Genome* 7: 767–9; Silverman, G. A. (1996), Methods in Molecular Biology, Vol. 54. D. Markie. Totowa, N.J., eds. Humana Press Inc. pp 65–68. All STSs shown to be associated with each YAC clone from the map were synthesized and tested to confirm that the clones were correct and aligned with overlapping YAC clones. Standard PCR conditions for physical mapping analyses were 10 mM Tris-HCl, 50 mM NaCl, 1.5 mM MgCl, 30 $\mu$M dNTPs, 0.5 $\mu$M of forward and reverse primers, and 50 ng of DNA in a 25 $\mu$L reaction volume. PCR thermocycles were 94° C. for 2 minutes, followed by 35–40 cycles of 94° C. for 10 seconds, 54° C. for 30 seconds, and 72° C. for 30 seconds with a 5 minute final extension at 72° C.

Example 4

Bacterial Artificial Chromosomes

BACs were identified and isolated from the PCR-based mouse BAC library available from Research Genetics using all known STSs and SSLPs found in the region on linkage and YAC maps. BAC DNA was prepared using purification columns by the recommended procedure (Magnum columns, Genome Systems, Inc). BAC end sequence was obtained using T7 and SP6 primers. Individual BAC insert sizes were determined by complete digestion of the BAC DNA with NotI and separating the fragments on a 1.0% agarose gel in 0.5×TBE circulating buffer. The field inversion gel electrophoresis (FIGE) program was 180 volts forward, 120 volts reverse, 0.1 seconds initial switching time linearly ramped to 3.5 seconds switching time for 16 hours.

Example 5

Simple Sequence Length Polymorphism (SSLP) Identification

BAC DNA was partially digested with Sau3A1 into fragments ranging from 1 to 3 Kb and subcloned into the Bam1 site of pUC18 with the Ready-To-Go cloning kit (Amersham Pharmacia Biotech). New repeats were identified by plating the subclone library, lifting duplicate Hybond-N membranes (Amersham Pharmacia Biotech), and hybridizing with $(CA)_{20}$ and $(AT)_{20}$ oligonucleotides end-labeled with $\gamma^{32}$P-ATP. Hybridized membranes were exposed to autoradiographic film. Clones producing a positive signal were sequenced and primer pairs were designed to amplify new repeat sequences. New SSLP markers were tested with control and recombinant mice to finely map the interval.

Example 6

Cosmid Subcloning

BAC 290J21 was partially digested with Sau3A1 into 30–40 Kb fragments which were subcloned into cosmids as per the instructions for the SuperCos 1 cosmid vector kit (Stratagene) and packaged with Gigapack m Gold Packaging Extract (Stratagene) using XL1-Blue mrf' competent cells. Cosmids were then aligned by amplification with all STSs across the region. Cosmid sequencing was performed by standard techniques using 1200 ng of cosmid DNA and 3.2 pmole of gene-specific mass1 oligos ranging from 18 to 24 nucleotides in length.

Example 7

Identifying and Cloning the mass1 Gene

The mass1 cDNA was identified by reverse transcription-PCR (RT-PCR) using primers developed from sequence of exons predicted by Genfinder. Total RNA was prepared from whole mouse brain of C57BL/6J, Frings and F1 mice with Trizol reagent as per instructions (Molecular Research Center, Inc.). The standard reverse transcription reaction conditions were 1.0 $\mu$g RNA, 15 ng random hexamers, 1×First Strand Buffer, 10 mM DTT, 1 mM dNTPs, 40 U RNAse Inhibitor, and 200 U Superscript II reverse transcriptase (Gibco BRL). First strand cDNAs were amplified using pfx DNA polymerase (Gibco BRL) and multiple reactions were sequenced for each. Since the entire gene was not contained within the genomic sequence that was generated, 5'- and 3'-RACE was used to identify the remaining cDNA sequences.

Example 8

Reverse Transcription-PCR

The RT reactions to determine tissue specificity of mass1 expression were performed as described in the previous section on samples from CF1 (Charles Rivers, Wilmington, Mass.), C57BL/6J (The Jackson Laboratory, Bar Harbor, Me.), or Frings mouse tissues and cells. The tissue panel samples were isolated from a single C57BL/6J mouse. The neuronal cDNA was produced from the pooled cellular extracts of 4–6 CF1 mouse cultured cortical neurons, and the astrocyte cDNA from CF1 astrocyte culture RNA extracted with Trizol reagent (Molecular Research Center, Inc). PCR conditions to amplify the cDNAs were 10 mM Tris-HCl, 50 mM KCl, 1.5 mM MgCl, 30 $\mu$M dNTPs, 0.5 $\mu$M of forward and reverse primers, and 1 $\mu$L of the cDNA in a 25 $\mu$L reaction volume. PCR thermocycles were 94° C. for 2 minutes, followed by 25 (β-actin primers) or 40 (mass1 primers) cycles of 94° C. for 10 seconds, 54° C. for 30 seconds, and 72° C. for 30 seconds with a 5 minute final extension at 72° C. The mass1 primers spanned from exon 22 to exon 23, the forward was 5' CAG AGG ATG GAT ACA GTA C 3' (SEQ ID NO: 29) and the reverse was 5' GTA ATC TCC TCC TTG AGT TG 3' (SEQ ID NO: 30) and the expected product size was 487 base pairs. The β-actin primers also spanned an intron and were forward 5' GCA GTG TGT TGG CAT AGA G 3' (SEQ ID NO: 31) and reverse 5' AGA TCC TGA CCG AGC GTG 3' (SEQ ID NO: 32) and the expected product size was 327 base pairs. PCR products for each tissue were mixed and separated by gel electrophoresis on 2% agarose gels in 1×TAE buffer at 120V, and the bands visualized by staining with ethidium bromide using an ultraviolet (UV) light source.

Example 9

Polymorphism and Mutation Identification

For SSCP, the mouse DNA samples A/J, AKRIJ, BALB/cJ, C57BU/6J, C3H/HeJ, CAST/EiJ, LP/J, NON/LtJ, NOD/LtJ, SPRET/EiJ, and DBA2/J were supplied by the Jackson Laboratory (Bar Harbor, Me.). The CF1 mice were supplied by Charles Rivers (Wilmington, Mass.), and the seizure-susceptible EL, EP, and SAS mice were supplied by Dr. T. Seyfried (Boston College, Boston, Mass.). PCR reactions were identical to those conditions listed above except 0.3 µL of $\alpha^{32}$P-dCTP was included in a 10 µL total reaction volume. A 30 µL aliquot of dilution buffer (0.1% SDS/10 mM EDTA in ddH$_2$O) was added to the PCR reactions. A 10 µL aliquot of the dilute PCR reaction was mixed with 10 µL of loading dye (bromophenol blue/xylene cyanol) and 2 µL samples were separated by non-denaturing electrophoresis on an 9% bis-acrylamide, 10% glycerol, nondenaturing gel at 20W for 14 hours at room temperature with a fan. The PCR forward primer sequence was 5' TTT ATT GTA GAG GAA CCT GAG 3' (SEQ ID NO: 33) and the reverse primer sequence was 5' GCC AGT AGC AAA CTG TCC 3' (SEQ ID NO: 34) and the expected product size was 126 base pairs. Exon 27 PCR products were sequenced to determine that the aberrant band was due to a single G deletion in the Frings mouse mass1 gene as shown for C57BL/6 and Frings mouse DNA.

Example 10

MASS1 Amino Acid Sequence Analysis

The amino acid sequence of MASS1 was deduced from the nucleotide sequence of the cloned mass1 cDNA by DNA Star. The amino acid sequence was compared to known proteins by BLAST sequence similarity searching available on the website of the National Center for Biotechnology Information of the National Institutes of Health. Identification of functional domains utilized PSORT II Prediction, Sequence Motif Search, Global and Domain Similarity Search, and Pattern Match.

Example 11

Identification and Mapping of a BAC Containing the hmass1 Gene

Human mass1 was detected by a relaxed RT-PCR. Several primer sets corresponding to different exons of mouse mass1 were used to amplify human fetal brain cDNA. PCR conditions were the same as in mouse amplifications with an exception of the annealing temperature of 47° C. These primers were used to identify a human genomic clone containing a part of the hMass1 gene (CITB human BAC library).

Human lymphoblast cultures were treated with 0.025 mg/ml cholcimid at 37° C. for 1.5 hr. Colcimid treated cultures were pelleted at 500×g at room temperature for 8 min. Pellets were then re-suspended with 0.075M KCl, 3 ml per pellet 15 minutes at room temperature. Cells were then fixed in 3:1 MeOH:acetic acid and stored at 4° C. Human BACs were labeled with spectrum orange using a nick translation kit per the manufacturers protocol (Vysis, Downers Grove, Ill.). Slides were prepared by dropping fixed cells onto glass slides and washing with excess fixative. The slides were then washed in acetic acid for 35 min at room temperature and dehydrated in 70%, 85%, and finally 100% EtOH (2 min each). Chromosomes were denatured in 70% formamide in 2×SSC at 74° C. for 5 minutes and slides were dehydrated again as above except in ice cold EtOH. Two µg of labeled probe was blocked with 2 µg of human Cot-1 DNA in Hybrisol VI (ONCOR, Gaithersburg, Md.). The probe mixture was denatured at 74° C. for 5 minutes and then pre-annealed at 37° C. for 15 min. Twelve µL of pre-annealed probe was applied per slide, a cover slip was added and edges were sealed with rubber cement. Slides were hybridized in a darkened, humidified chamber for 16 hr at 37° C. Hybridized slides were then washed in 0.4×SSC containing 0.1% Tween-20 at 74° C. for 2 min, followed by 1 min at room temperature in 2×SSC. Slides were allowed to dry in the ark at room temperature and were stained with DAPI (Vector labs, Burlingame, Calif.) for chromosome visualization.

Summary

In summary, a novel gene which is associated with the Frings phenotype in mice has been isolated and characterized. The gene is known as the Monogenic Audiogenic Seizure-susceptible gene or mass1. The product of the mass1 gene is designated MASS1. Nucleic acid molecules that encode for MASS1 have been identified and purified. The sequence of murine mass1 can be found at SEQ ID NO: 1, and the sequence of human mass1 can be found at SEQ ID NO: 3. Mammalian genes encoding a MASS1 protein are also provided. The invention also provides recombinant vectors comprising nucleic acid molecules that code for a MASS1 protein. These vectors can be plasmids. In certain embodiments, the vectors are prokaryotic or eukaryotic expression vectors. The nucleic acid coding for MASS1 can be linked to a heterologous promoter. The invention also relates to transgenic animals in which one or both alleles of the endogenous mass1 gene is mutated.

The invention may be embodied in other specific forms without departing from its essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An isolated and purified nucleic acid, the nucleic acid comprising nucleotides which code for the amino acid sequence of SEQ ID NO: 4.

2. A recombinant vector comprising the nucleic acid molecule of claim 1.

3. The recombinant vector of claim 2, wherein the recombinant vector is a plasmid.

4. The recombinant vector of claim 2, wherein the recombinant vector is a prokaryotic or eukaryotic expression vector.

5. The recombinant vector of claim 2, wherein the nucleic acid molecule is operably linked to a heterologous promoter.

6. A host cell comprising the vector of claim 2.

7. The host cell of claim 6, wherein the host cell is a eukaryotic host cell.

8. The host cell of claim 6, wherein the host cell is a prokaryotic host cell.

9. An isolated and purified nucleic acid which codes for human monogenic audiogenic seizure-susceptible protein, the nucleic acid comprising the nucleotide sequence of SEQ ID NO: 3.

10. An isolated and purified nucleic acid comprising the nucleotide sequence of SEQ ID NO: 3 or a nucleotide sequence complementary to the nucleotide sequence of SEQ ID NO: 3.

11. A recombinant vector comprising the nucleic acid molecule of claim 10.

12. The recombinant vector of claim 11, wherein the recombinant vector is a plasmid.

13. The recombinant vector of claim 11, wherein the recombinant vector is a prokaryotic or eukaryotic expression vector.

14. The recombinant vector of claim 11, wherein the nucleic acid molecule is operably linked to a heterologous promoter.

15. A host cell comprising the vector of claim 11.

16. The host cell of claim 15, wherein the host cell is a eukaryotic host cell.

17. The host cell of claim 15, wherein the host cell is a prokaryotic host cell.

18. An isolated and purified nucleic acid, the nucleic acid comprising nucleotides which code for the amino acid sequence of SEQ ID NO: 2.

19. A recombinant vector comprising the nucleic acid molecule of claim 18.

20. The recombinant vector of claim 19, wherein the recombinant vector is a plasmid.

21. The recombinant vector of claim 19, wherein the recombinant vector is a prokaryotic or eukaryotic expression vector.

22. The recombinant vector of claim 19, wherein the nucleic acid molecule is operably linked to a heterologous promoter.

23. A host cell comprising the vector of claim 19.

24. The host cell of claim 23, wherein the host cell is a eukaryotic host cell.

25. The host cell of claim 23, wherein the host cell is a prokaryotic host cell.

26. An isolated and purified nucleic acid which codes for murine microgenic audiogenic seizure-susceptible protein, the nucleic acid comprising the nucleotide sequence of SEQ ID NO: 1.

27. An isolated and purified nucleic acid comprising the nucleotide sequence of SEQ ID NO: 1 or a nucleotide sequence complementary to the nucleotide sequence of SEQ ID NO: 1.

28. A recombinant vector comprising the nucleic acid molecule of claim 27.

29. The recombinant vector of claim 28, wherein the recombinant vector is a plasmid.

30. The recombinant vector of claim 28, wherein the recombinant vector is a prokaryotic or eukaryotic expression vector.

31. The recombinant vector of claim 28, wherein the nucleic acid molecule is operably linked to a heterologous promoter.

32. A host cell comprising the vector of claim 28.

33. The host cell of claim 32, wherein the host cell is a eukaryotic host cell.

34. The host cell of claim 32, wherein the host cell is a prokaryotic host cell.

* * * * *

UNITED STATES PATENT AND TRADEMARK OFFICE
CERTIFICATE OF CORRECTION

PATENT NO. : 6,794,187 B2　　　　　　　　　　　　　　　　　　　　　　Page 1 of 1
DATED : September 21, 2004
INVENTOR(S) : Louis Ptacek et al.

It is certified that error appears in the above-identified patent and that said Letters Patent is hereby corrected as shown below:

Column 1,
Line 15, please add the following:
-- STATEMENT REGARDING FEDERALLY SPONSERED RESEARCH
This invention was made with government support under grant number RO1 NS38616 awarded by the National Institutes of Health. The Government has certain rights to this invention --.

Signed and Sealed this

First Day of February, 2005

JON W. DUDAS
*Director of the United States Patent and Trademark Office*